US012408978B2

(12) United States Patent
Panescu et al.

(10) Patent No.: US 12,408,978 B2
(45) Date of Patent: Sep. 9, 2025

(54) DEVICES AND METHODS FOR TREATING LUNG TUMORS

(71) Applicant: Zidan Medical Inc., New York, NY (US)

(72) Inventors: Dorin Panescu, San Jose, CA (US); Shashank Raina, Santa Clara, CA (US); Mark Gelfand, New York, NY (US); Mark Leung, Duncan (CA); Simplicio Velilla, Santa Clara, CA (US)

(73) Assignee: ZIDAN MEDICAL, INC., New York, NY (US)

( * ) Notice: Subject to any disclaimer, the term of this patent is extended or adjusted under 35 U.S.C. 154(b) by 0 days.

(21) Appl. No.: 18/602,921

(22) Filed: Mar. 12, 2024

(65) Prior Publication Data
US 2024/0252237 A1  Aug. 1, 2024

Related U.S. Application Data

(63) Continuation of application No. 17/088,051, filed on Nov. 3, 2020, now Pat. No. 11,925,409, which is a
(Continued)

(30) Foreign Application Priority Data

Apr. 9, 2018  (CN) .......................... 201810310511.1

(51) Int. Cl.
*A61B 18/14* (2006.01)
*A61B 18/00* (2006.01)
(Continued)

(52) U.S. Cl.
CPC .......... *A61B 18/1492* (2013.01); *A61B 34/20* (2016.02); *A61B 2018/0022* (2013.01);
(Continued)

(58) Field of Classification Search
CPC ........ A61B 18/1492; A61B 2018/0022; A61B 2018/00285; A61B 2018/00541;
(Continued)

(56) References Cited

U.S. PATENT DOCUMENTS 4,920,978 A   5/1990 Colvin
5,585,362 A   12/1996 Wilson et al.
(Continued)

FOREIGN PATENT DOCUMENTS

CN  201356648  12/2009
CN  103037791   4/2013
(Continued)

OTHER PUBLICATIONS

Hiroshi Anai, Effects of Blood Flow and/or Ventilation Restriction on Radiofrequency Coagulation Size in the Lung: An Experimental Study in Swine, Cardiovasc Intervent Radiol. (2006), 29:838-845.
(Continued)

*Primary Examiner* — Tigist S Demie
(74) *Attorney, Agent, or Firm* — Nixon & Vanderhye P.C.

(57) ABSTRACT

A method to treat a human patient including: advancing a catheter through a natural airway of the patient and positioning a distal portion of the catheter in the natural airway of a lung of the patient to a target region in the lung, injecting a conductive hypertonic saline solution having a concentration of at least 5% of sodium chloride by weight/volume from the distal portion of the catheter into the target region; delivering energy from the distal portion into the conductive hypertonic saline solution in the target region, wherein the energy heats the liquid in the portion of the airway, and ablating the target region with the heated liquid.

32 Claims, 17 Drawing Sheets

Related U.S. Application Data continuation of application No. 16/521,334, filed on Jul. 24, 2019, now Pat. No. 10,842,560, which is a continuation of application No. PCT/US2018/049991, filed on Sep. 7, 2018.

(60) Provisional application No. 62/650,246, filed on Mar. 29, 2018, provisional application No. 62/631,225, filed on Feb. 15, 2018, provisional application No. 62/555,675, filed on Sep. 8, 2017.

(51) Int. Cl.
*A61B 18/04* (2006.01)
*A61B 34/20* (2016.01)

(52) U.S. Cl.
CPC ........ *A61B 2018/00541* (2013.01); *A61B 2018/00577* (2013.01); *A61B 2018/00642* (2013.01); *A61B 2018/00791* (2013.01); *A61B 2018/00875* (2013.01); *A61B 2018/00982* (2013.01); *A61B 2018/048* (2013.01); *A61B 2018/1425* (2013.01); *A61B 2018/1467* (2013.01); *A61B 2018/1472* (2013.01); *A61B 2034/2051* (2016.02); *A61B 2034/2061* (2016.02); *A61B 2034/2063* (2016.02); *A61B 2218/002* (2013.01); *A61B 2218/007* (2013.01)

(58) Field of Classification Search
CPC .......... A61B 2018/00577; A61B 2018/00642; A61B 2018/00648; A61B 2018/00702; A61B 2018/00744; A61B 2018/00791; A61B 2018/00875; A61B 2018/00982; A61B 2018/048; A61B 2018/1425; A61B 2018/1467; A61B 2018/1472; A61B 2034/2051; A61B 2034/2061; A61B 2034/2063; A61B 2218/002; A61B 2218/007; A61B 34/20
See application file for complete search history.

(56) References Cited

U.S. PATENT DOCUMENTS

| | | |
|---|---|---|
| 5,722,403 A | 3/1998 | McGee et al. |
| 5,740,808 A | 4/1998 | Panescu et al. |
| 5,868,736 A | 2/1999 | Swanson et al. |
| 6,003,517 A | 12/1999 | Sheffield et al. |
| 6,258,100 B1 | 7/2001 | Alferness et al. |
| 6,293,951 B1 | 9/2001 | Alferness et al. |
| 6,315,776 B1 | 11/2001 | Edwards et al. |
| 6,402,742 B1 | 6/2002 | Blewett et al. |
| 6,409,722 B1 | 6/2002 | Hoey et al. |
| 6,537,272 B2 | 3/2003 | Christopherson et al. |
| 6,702,811 B2 | 3/2004 | Stewart et al. |
| 6,736,810 B2 | 5/2004 | Hoey et al. |
| 6,770,070 B1 | 8/2004 | Balbierz |
| 6,849,073 B2 | 2/2005 | Hoey et al. |
| 6,971,394 B2 | 12/2005 | Sliwa, Jr. et al. |
| 7,115,139 B2 | 10/2006 | McClurken et al. |
| 7,128,747 B2 | 10/2006 | Ginn |
| 7,169,144 B2 | 1/2007 | Hoey et al. |
| 7,187,971 B2 | 3/2007 | Sommer et al. |
| 7,247,155 B2 | 7/2007 | Hoey et al. |
| 7,344,533 B2 | 3/2008 | Pearson et al. |
| 7,412,977 B2 | 8/2008 | Fields et al. |
| 7,628,789 B2 | 12/2009 | Soltesz et al. |
| 7,771,472 B2 | 8/2010 | Hendricksen et al. |
| 7,892,229 B2 | 2/2011 | Shadduck et al. |
| 7,913,698 B2 | 3/2011 | Barry et al. |
| 7,921,855 B2 | 4/2011 | Danek et al. |
| 7,931,647 B2 | 4/2011 | Wizeman et al. |
| 7,949,407 B2 | 5/2011 | Kaplan et al. |
| 8,088,127 B2 | 1/2012 | Mayse et al. |
| 8,187,268 B2 | 5/2012 | Godara et al. |
| 8,226,575 B2 | 7/2012 | Levy |
| 8,262,581 B2 | 9/2012 | Eumura et al. |
| 8,308,722 B2 | 11/2012 | Ormsby et al. |
| 8,568,403 B2 | 10/2013 | Soltesz et al. |
| 8,709,034 B2 | 4/2014 | Keast et al. |
| 8,753,381 B2 | 6/2014 | Henriksson et al. |
| 8,858,549 B2 | 10/2014 | Shadduck et al. |
| 8,911,430 B2 | 12/2014 | Hoey et al. |
| 8,932,316 B2 | 1/2015 | Keast et al. |
| 9,044,254 B2 | 6/2015 | Ladtkow et al. |
| 9,108,052 B2 | 8/2015 | Jarrard |
| 9,113,944 B2 | 8/2015 | Shadduck |
| 9,161,808 B2 | 10/2015 | Nollert |
| 9,421,070 B2 | 8/2016 | Keast et al. |
| 9,463,064 B2 | 10/2016 | Subramaniam et al. |
| 9,517,103 B2 | 12/2016 | Panescu et al. |
| 9,522,036 B2 | 12/2016 | Panescu et al. |
| 9,522,037 B2 | 12/2016 | Panescu et al. |
| 9,526,574 B2 | 12/2016 | Wang et al. |
| 9,566,115 B2 | 2/2017 | Van Der Weide et al. |
| 9,592,092 B2 | 3/2017 | Panescu et al. |
| 9,603,659 B2 | 3/2017 | Subramaniam et al. |
| 9,636,164 B2 | 5/2017 | Panescu et al. |
| 9,668,809 B2 | 6/2017 | Mayse et al. |
| 9,743,984 B1 | 8/2017 | Curley et al. |
| 9,770,282 B2 | 9/2017 | Hoey et al. |
| 9,861,440 B2 | 1/2018 | Van Der Weide et al. |
| 9,867,648 B2 | 1/2018 | Mulcahey et al. |
| 9,872,729 B2 | 1/2018 | Van Der Weide et al. |
| 9,884,201 B2 | 2/2018 | Henriksson et al. |
| 9,901,384 B2 | 2/2018 | Clark et al. |
| 9,943,353 B2 | 4/2018 | Hoey et al. |
| 9,956,032 B1 | 5/2018 | Cosman et al. |
| 9,993,291 B2 | 6/2018 | Cao et al. |
| 10,231,770 B2 | 3/2019 | Druma |
| 10,376,299 B2 | 8/2019 | Avitall et al. |
| 2002/0165448 A1 | 11/2002 | Ben-Haim et al. |
| 2003/0228344 A1 | 12/2003 | Fields et al. |
| 2006/0195079 A1* | 8/2006 | Eberl ................ A61B 18/1492 606/49 |
| 2006/0254600 A1 | 11/2006 | Danek et al. |
| 2007/0265687 A1 | 11/2007 | Deem et al. |
| 2008/0051756 A1 | 2/2008 | Makower et al. |
| 2009/0099560 A1* | 4/2009 | Rioux ................ A61M 25/1011 606/41 |
| 2011/0301587 A1 | 12/2011 | Deem et al. |
| 2012/0053485 A1 | 3/2012 | Bloom |
| 2012/0143099 A1 | 6/2012 | Daniels et al. |
| 2013/0046296 A1 | 2/2013 | Laufer |
| 2013/0310822 A1 | 11/2013 | Mayse et al. |
| 2013/0317339 A1 | 11/2013 | Waldstreicher et al. |
| 2013/0338530 A1 | 12/2013 | Kassab |
| 2014/0018605 A1 | 1/2014 | Soltesz et al. |
| 2014/0046174 A1 | 2/2014 | Ladtkow et al. |
| 2014/0088588 A1 | 3/2014 | Jarrard |
| 2014/0276709 A1 | 9/2014 | Wittenberger et al. |
| 2015/0119877 A1 | 4/2015 | Jameson et al. |
| 2015/0157382 A1 | 6/2015 | Avitall et al. |
| 2015/0265331 A1 | 9/2015 | Fleury et al. |
| 2015/0265342 A1 | 9/2015 | Long et al. |
| 2016/0051327 A1 | 2/2016 | Brannan |
| 2016/0151103 A1 | 6/2016 | Henne et al. |
| 2016/0175041 A1 | 6/2016 | Govari et al. |
| 2016/0184013 A1 | 6/2016 | Brannan et al. |
| 2016/0287912 A1 | 10/2016 | Warnking |
| 2016/0310210 A1 | 10/2016 | Harshman et al. |
| 2017/0079519 A1 | 3/2017 | Sung et al. |
| 2017/0112558 A1 | 4/2017 | Sara |
| 2017/0128039 A1 | 5/2017 | Waldstreicher et al. |
| 2017/0135754 A1 | 5/2017 | Gliner |
| 2017/0325837 A1 | 11/2017 | Thompson et al. |
| 2017/0325894 A1 | 11/2017 | Krimsky |
| 2018/0161142 A1 | 6/2018 | Finger et al. |

(56) References Cited

U.S. PATENT DOCUMENTS

| | | | |
|---|---|---|---|
| 2018/0184982 A1 | 7/2018 | Basu et al. | |
| 2018/0296264 A1 | 10/2018 | DeSimone | |

FOREIGN PATENT DOCUMENTS

| | | |
|---|---|---|
| CN | 103118613 | 5/2013 |
| CN | 203122582 | 8/2013 |
| CN | 203341811 | 12/2013 |
| CN | 103892907 | 7/2014 |
| CN | 103917185 | 7/2014 |
| CN | 103987336 | 8/2014 |
| CN | 103371865 | 4/2015 |
| CN | 104507407 | 4/2015 |
| CN | 104519821 | 4/2015 |
| CN | 104546117 | 4/2015 |
| CN | 102639077 | 5/2015 |
| CN | 102940524 | 9/2015 |
| CN | 105188585 | 12/2015 |
| CN | 105555225 | 5/2016 |
| CN | 105640642 | 6/2016 |
| CN | 105708544 | 6/2016 |
| CN | 105828736 | 8/2016 |
| CN | 105939758 | 9/2016 |
| CN | 105943159 | 9/2016 |
| CN | 106037927 | 10/2016 |
| CN | 106061421 | 10/2016 |
| CN | 205672073 | 11/2016 |
| CN | 106572884 | 4/2017 |
| CN | 106963474 | 7/2017 |
| CN | 107106194 | 8/2017 |
| CN | 107106235 | 8/2017 |
| CN | 107307901 | 11/2017 |
| CN | 107456269 | 12/2017 |
| CN | 104939920 | 2/2018 |
| CN | 105147389 | 3/2018 |
| CN | 104470454 | 6/2018 |
| CN | 108135496 | 6/2018 |
| CN | 108272505 | 7/2018 |
| CN | 109464186 | 3/2019 |
| EP | 2180917 | 5/2010 |
| EP | 1450712 | 5/2011 |
| EP | 3184066 | 6/2017 |
| WO | 2009/015278 | 1/2009 |
| WO | 2010141417 | 12/2010 |
| WO | 2014052199 | 4/2014 |
| WO | 2014/197632 | 12/2014 |
| WO | 2015006729 | 1/2015 |
| WO | 2016029022 | 2/2016 |
| WO | 2016090175 | 6/2016 |
| WO | 2016109437 | 7/2016 |
| WO | 2017062753 | 4/2017 |
| WO | 2019051251 | 3/2019 |

OTHER PUBLICATIONS

Tae Sung et al., "Excessive Hyperthermic Necrosis of a Pulmonary Lobe After Hypertonic Saline-Enhanced Monopolar Radiofrequency Ablation", Cardiovasc Intervent Radiol. (2006), 29:160-163.

Tomonobu Koizumi et al, "Clinical Experience of Bronchoscopy-Guided Radiofrequency Ablation for Peripheral-Type Lung Cancer", Case Reports in Oncological Medicine, vol. 2013, Article ID 515160, http://dx.doi.org/10.1155/2013/515160, 5 pages.

Fumiyoshi Oshima et al, Lung Radiofrequency Ablation with and without Bronchial Occlusion: Experimental Study in Porcine Lungs, Laboratory Investigations, J Vasc Interv Radiol 2004; 15:1451-1456.

Invitation to Pay Additional Fees issued in PCT/US2020/019784 mailed Jul. 6, 2020, 13 pages.

International Search Report cited in WO 2019/051251 mailed Jan. 7, 2019, 3 pages.

Partial Search Report cited in EP 19189086.2 mailed Mar. 31, 2020, 11 pages.

U.S. Appl. No. 16/521,115, filed Jul. 24, 2019.

D. Scott Cohen et al., Case Reports, "Pulmonary Edema Associated With Salt Water Near-Drowning: New Insights", Am Rev Respir Dis 1992; 146:794-796.

Lt. Commander Carl Edmonds, "A Salt Water Aspiration Syndrome" Downloaded from https://academic.oup.com/milmed/article-abstract/135/9/779/4919434 by Washington University in St. Louis user on Feb. 14, 2019, pp. 779-785.

Tatsuhiko Iishi et al., Acta Medica Okayama, "Infusion of Hypertonic Saline Into the Lung Parenchyma During Radiofrequency Ablation of the Lungs with Multitined Expandable Electrodes: Results Using a Porcine Model", vol. 63, Issue 3, Jun. 2009, 10 pages.

Tae Sung Kim et al., "Excessive Hyperthermic Necrosis of a Pulmonary Lobe After Hypertonic Saline-Enhanced Monopolar Radiofrequency Ablation", Cardiovasc Intervent Radiol (2006) 29, pp. 160-163.

* cited by examiner

DEVICES AND METHODS FOR TREATING LUNG TUMORS

RELATED APPLICATIONS

This application is a continuation of U.S. patent application Ser. No. 17/088,051 (now U.S. Pat. No. 11,925,409), filed Nov. 3, 2020, which is continuation of U.S. patent application Ser. No. 16/521,334 filed Jul. 24, 2019 (now U.S. Pat. No. 10,842,560), which is a by-pass continuation under 35 U.S.C. §§ 111 and 120 of PCT/US2018/049991 filed Sep. 7, 2018, and claims priority to U.S. Provisional Applications 62/555,675, filed Sep. 8, 2017; 62/631,225 filed Feb. 15, 2018 and 62/650,246 filed Mar. 29, 2018, and to Chinese Patent Application 201810310511.1 filed Apr. 9, 2018. The entire contents of each of these PCT, provisional and Chinese applications are incorporated by reference.

TECHNICAL FIELD

The present disclosure is directed generally to devices and methods for ablating malignant lung tumors and more particularly to ablating lung tumors with an approach through the patient's airway.

BACKGROUND

Lung cancer remains the leading cause of cancer-related deaths in the world. In fact, lung cancer is responsible for more deaths each year in this country than breast cancer, colon cancer, and prostate cancer combined. Non-small cell lung cancer (NSCLC) is the most common type of lung cancer; it is named for the type of cell within the lung where the cancer originates. Approximately 75 to 80% of individuals with lung cancer have NSCLC. Early NSCLC refers to cancer that has not spread widely outside of its site of origin. The earlier lung cancer is detected and treated, the better the outcome. The current standard treatment for early lung cancer consists of the surgical removal of as much of the cancer as possible followed by chemotherapy and/or radiation therapy.

Surgical removal of a lung or lobe is the gold standard treatment for treating stage 1 or 2 non-small-cell-lung-cancer (NSCLC). Unfortunately, only about 15% to 30% of patients diagnosed with lung carcinoma each year are surgical candidates. Particularly, many patients with concurrent Chronic Obstructive Pulmonary Disease (COPD) are not considered suitable for surgery.

Percutaneous pulmonary radiofrequency ablation (RFA) with a needle electrode inserted through the chest wall under CT guidance has become an increasingly adopted treatment option for primary and metastatic lung tumours. The immediate technical success rate is over 95%, with a low periprocedural mortality rate and 8 to 12% major complication rate. Pneumothorax represents the most frequent complication, but requires a chest tube drain in less than 10% of cases. Sustained complete tumour response has been reported in 85% to 90% of target lesions.

Bronchoscopic ablation of lung tumors is perceived by many as the next frontier in non-surgical thermal tumor ablation but has been held back by lack of specialized equipment for creation of large enough volume of destroyed tissue at the targeted site. This limitation is additionally challenged by the necessity to operate through the working channel of the bronchoscope, by the difficulty of endoscopically navigating the ablation electrodes to targeted tumors and by the specific properties of lung tissue that is amply perfused by blood flow, cooled by perfusion, evaporation and convection, and incorporates a large volume of air that increases the RF path electrical impedance and can also deform the volume of targeted tissue in phase with breathing. The latter consideration led to research preference being given to microwave energy, since microwave energy travels through air well. However, there is an advantage of simplicity and efficiency in RF heating of tissues that are appreciated in the field.

In light of the foregoing there remains a need for improvements to RF energy delivery methods and devices that prove suitability for bronchoscope-delivered ablation of lung tumors. It is further desired for the devices to be flexible and relatively soft and fit in working channels that are small in diameter, preferable less than 2 mm, in order to reach tumors that are closer to the periphery of the lung.

SUMMARY

This disclosure is related to methods, devices, and systems for transbronchial ablation of a lung tumor. Aspects of the disclosure include:

Devices and systems suitable for infusing conductive fluid (e.g. HTS) into the airway through the endobronchial ablation catheter to reduce tissue impedance and increase the effective RF energy delivery electrode size.

Occluding the airway leading to the targeted tumor;

Surrounding or penetrating a tumor, peripheral or central, with ablation electrodes;

Ablating the tumor with RF ablation energy using monopolar, multiple monopolar, bipolar, multi-polar and multiphasic RF configurations;

Ablating the tumor with RF ablation energy and irrigating the RF electrodes, with normal or hypertonic saline, and controlling the RF ablation energy with feedback from temperature sensors, irrigation saline concentration, temperature or flow rate or impedance;

Collapsing, compressing, volume reducing or partially collapsing a portion of a lung comprising a tumor to ablate the tumor;

Placing ablation catheters over guide wires and exchanging bronchoscope;

Placement of electrodes in airways using over the wire exchange of a bronchoscope and electrode catheter;

Placement of needle electrodes in tumors using spring-loaded or push-pull catheter handle designs;

Exchanging a guided biopsy tool with a non-guided or guided ablation tool upon a positive on-site biopsy result and maneuvering to the same biopsied location under fluoroscopy or ultrasound guidance;

Decreasing blood flow to the targeted region of lung by decreasing oxygen in said region and causing local hypoxic vasoconstriction prior to or during delivery of ablation energy.

Endobronchial navigation using CT image data to create a navigation plan to facilitate advancing an ablation catheter through a bronchoscope and a branch of a bronchus of a patient towards the nodule. Electromagnetic tracking may also be utilized in conjunction with the CT data to facilitate guiding the ablation catheter through the branch of the bronchus to the nodule. The ablation catheter may be positioned within one of the airways of the branched luminal networks adjacent to or within the nodule or point of interest. Once in position, fluoroscopy may be used to visualize the ablation catheter as it is further maneuvered towards the nodule or point of interest. Other imaging techniques, such as MRI, ultrasound, etc., may be used in conjunction with, or in lieu of, fluoroscopy or CT in combination with navigational bronchoscopy. Optionally, the endobronchial ablation catheter may be fitted with sensors (e.g. 3D electromagnetic coils) compatible with the navigational bronchoscopy system available on site.

DETAILED DESCRIPTION

The present disclosure is directed generally to devices and methods for ablating malignant lung tumors and more particularly to ablating lung tumors with an approach through the patient's airway. An approach through the patient's airway may also be referred to as a transbronchial or endobronchial approach and comprises delivering medical devices through passageways by which air passes through the nose or mouth to the alveoli of the lungs. The term airway refers to any of the anatomical lumens of the respiratory system through which air passes including the trachea, bronchi, and bronchioles.

Figure 1:
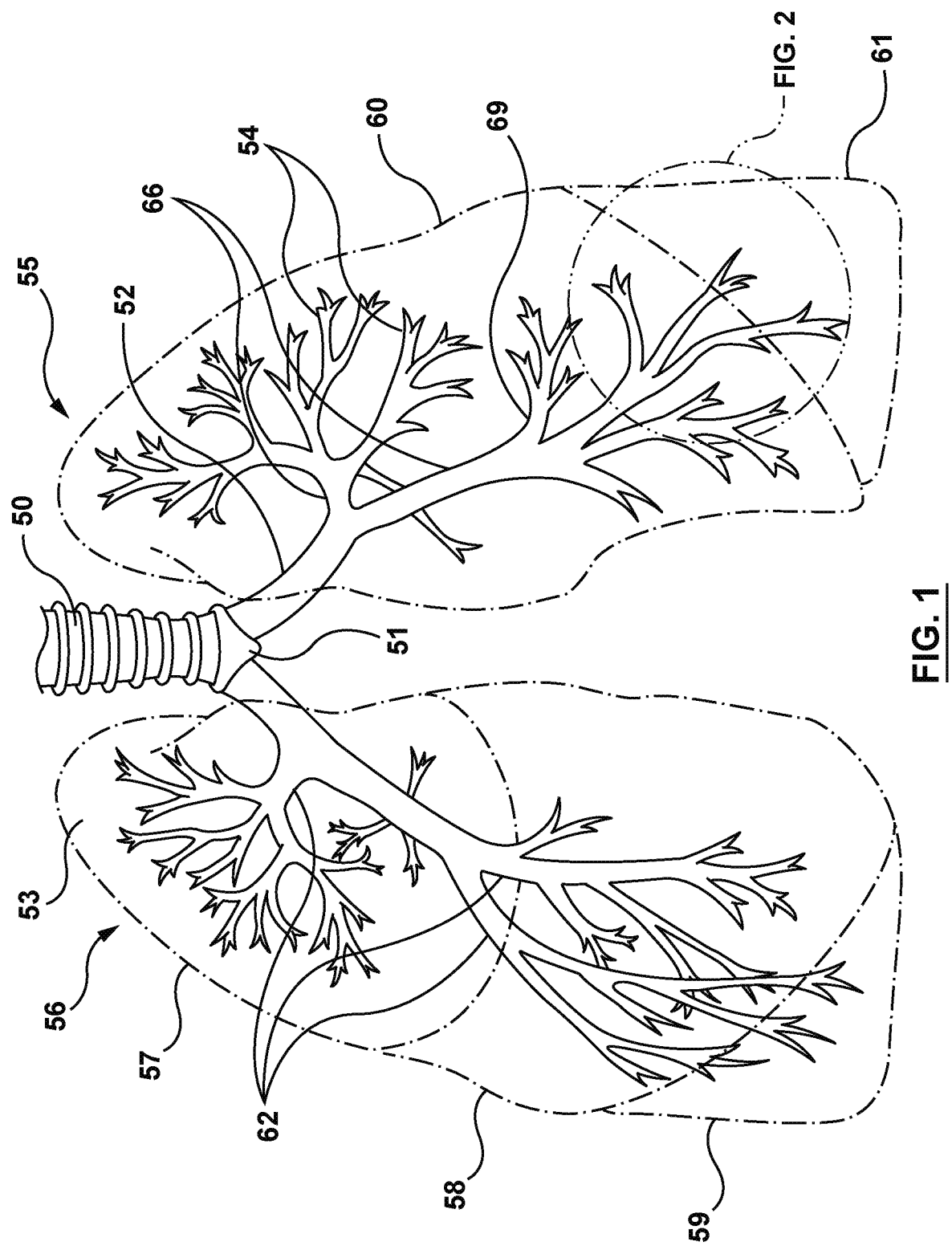
FIG. 1 is a schematic illustration of part of a human respiratory system.
Figure 2:
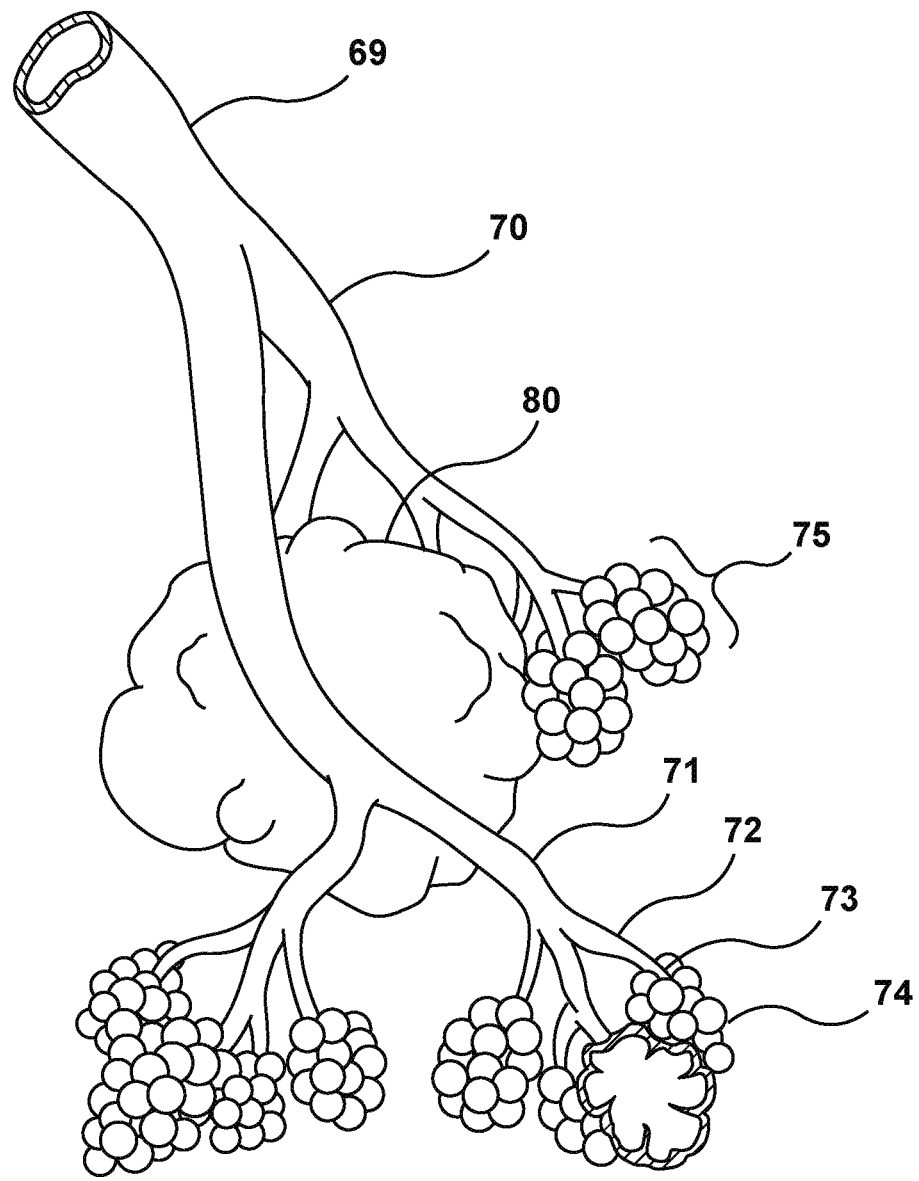
FIG. 2 is a closer view of a section of FIG. 1.

FIG. 1 is a schematic illustration of part of a patient's respiratory system including the trachea 50, carina of trachea 51, left main bronchus 52, right main bronchus 53, bronchioles 54, alveoli (not shown, residing in bunches at the end of bronchioles), left lung 55, right lung 56. The right main bronchus subdivides into three secondary bronchi 62 (also known as lobar bronchi), which deliver oxygen to the three lobes of the right lung—the superior lobe 57, middle lobe 58, and inferior lobe 59. The left main bronchus divides into two secondary 66 or lobar bronchi to deliver air to the two lobes of the left lung—the superior 60 and the inferior 61 lobes. The secondary bronchi divide further into tertiary bronchi 69, (also known as segmental bronchi), each of which supplies a bronchopulmonary segment. A bronchopulmonary segment is a division of a lung separated from the rest of the lung by a septum of connective tissue (not shown). As shown in FIG. 2 the tertiary bronchi 69 divide into many primary bronchioles 70, which divide into terminal bronchioles 71, each of which then gives rise to several respiratory bronchioles 72, which go on to divide into two to eleven alveolar ducts 73. There are five or six alveolar sacs 75 associated with each alveolar duct. Alveolar sacs are made up of several alveoli 74. The alveolus 74 is the basic anatomical unit of gas exchange in the lung. FIG. 2 also shows a peripherally located tumor 80 positioned in a space external to and amongst the bronchioles. A targeted tumor 80 may reside peripherally, centrally, or within a lymph node or airway wall of a lung or mediastinum.

There are two major types of lung cancer, non-small cell lung cancer (NSCLC) and small cell lung cancer (SCLC). Non-small cell lung cancer accounts for about 85 percent of lung cancers and includes: Adenocarcinoma, the most common form of lung cancer in the United States among both men and women, are formed from glandular structures in epithelial tissue and usually forms in peripheral areas of the lung; Squamous cell carcinoma, which accounts for 25 percent of all lung cancers and is more typically centrally located; Large cell carcinoma, which accounts for about 10 percent of NSCLC tumors. The focus of this disclosure is on treating NSCLC, which may occur peripherally among bronchioles, centrally among bronchi, or in lymph nodes.

An aspect of the disclosure provides a method for treating a lung tumor of a patient. A pathway to a point of interest in a lung of a patient is generated. It is anticipated that in the majority of patients with a solitary nodule an airway can be identified on CT leading to the target suitable for positioning of an ablation energy delivery element proximate, for example within 1 cm, of the target. Using a pre-acquired CT as a map a flexible instrument can be threaded through the airways by a bronchoscopist using known and existing tools. In one embodiment, an extended working channel is advanced through the airway into the lung and along the pathway to the point of interest. The extended working channel is positioned in a substantially fixed orientation at the point of interest. Anchoring mechanisms may be used to secure stability of the channel. A catheter may be advanced though the extended working channel to the targeted region of the lung. A working channel may be for example a lumen through a delivery sheath or through a bronchoscope, both of which may be steerable or incorporate a guidewire lumen. A portion of the lung containing the targeted region may be occluded and at least partially collapsed, for example by occluding an airway feeding the portion (e.g., using at least an occluding balloon on the catheter) and applying negative pressure to the lung portion or other means for collapsing a portion of lung disclosed herein. To confirm partial collapse of the portion of lung, electrodes on the catheter may be used to measure tissue impedance and phase. A complete collapse of the targeted lung portion, while desired, is not necessary. Experimental observations show that a partial collapse of the targeted lung portion, which produces a 20% decrease in the respective bipolar impedance, is sufficient for the purpose of facilitating effective ablation energy delivery. The lung tissue is treated with the ablation catheter at the targeted region of the lung by injecting hypertonic saline through the catheter into the collapsed portion of lung and applying RF energy from one or more electrodes on the catheter. Optionally, more than one ablation catheter may be delivered to the targeted region of lung and an RF circuit may be made between electrode(s) on a first catheter to electrode(s) on a second catheter. In the presented embodiments of this disclosure RF electrodes are used to deliver ablation energy.

An extended working channel may be positioned within a patient, optionally through a bronchoscope or as part of a bronchoscope. A locatable guide may be positioned within the extended working channel for positioning the extended working channel to the point of interest. Biopsy tools may be advanced to the point of interest. Prior to advancing the biopsy tool through the extended working channel, the locatable guide may be removed from the extended working channel. Alternatively, navigation-guided extended working channels may be used in conjunction with 3-D navigation systems, such those offered by Veran Medical or superDimension™ (Medtronic). The lung tissue may be biopsied. If the biopsy is confirmed positive, then the lung tissue may be ablated. The biopsy tool is retracted and replaced with an ablation catheter or tool comprising at least one energy delivery element. This method may facilitate positioning of the energy delivery elements of the ablation catheter or tool at the same place where the biopsy is taken. Prior to treating the lung tissue, the placement of the ablation catheter at the point of interest may be confirmed, for example visually using a bronchoscope and identifying the point of interest with respect to elements of the airway. The lung tissue or tumor may be penetrated at the point of interest. Effective treatment of the lung tissue may be confirmed.

With the current resolution of CT scanners, at least seven or eight, likely more, generations of airways can be imaged and evaluated. There are reasons to believe that the imaging resolution will rapidly improve further. If the trachea is the beginning point and if a pulmonary parenchymal nodule is the targeted end-point, then appropriate software can interrogate the three-dimensional image data set and provide a pathway or several pathways through the adjacent airways to the target. The bronchoscopist can follow this pathway during a real or navigational bronchoscopy procedure and the correct airway pathway to the nodule can be quickly cannulated using a wire, a bronchoscope and a thin wall polymer tube or channel, or sensed/navigational bronchoscopy instruments.

Once the access channel is in place, then multiple probes can be placed either to biopsy, or to ablate the identified tumor. Ultrathin bronchoscopes can be used in a similar manner. In conjunction with navigational bronschoscopy tools, using these sorts of approaches, majority of peripheral lung lesions can be destroyed.

Currently available fiberoptic bronchoscopes (FOBs) have an illumination fiberoptic bundle and imaging fiberoptics or a camera. Except for the very few "ultrathin" bronchoscopes, there is also a channel for suction of secretions and blood, for the passage of topical medication and fluid for washing, and for the passage of various instruments for diagnostic retrieval of tissues or for therapeutic procedures. A typical diagnostic bronchoscope has an outer diameter of 5.0 to 5.5 mm and an operating channel of 2.0 to 2.2 mm. This caliber channel admits most cytology brushes, bronchial biopsy forceps, and transbronchial aspiration needles with sheathed outer diameters between 1.8 and 2.0 mm. Smaller bronchoscopes, in the range of 3.0 to 4.0 mm at the outer diameter and correspondingly smaller channels, are usually given a "P" designation (for pediatrics), but they can be used in the adult airways. Newer generations of slim video and fiberoptic bronchoscopes have a 2.0 mm operating channel with a 4.0 mm outer diameter. The one disadvantage of these bronchoscopes is the sacrifice of a smaller image area because of fewer optical bundles. The ultrathin bronchoscopes generally have outer diameters smaller than 3 mm. For example, Olympus models BF-XP40 and BF-XP160F (Olympus America, Center Valley, PA) have outer diameters of 2.8 mm and operating channels of 1.2 mm. Special instruments (e.g., reusable cytology brush and forceps) of the proper calibre are available for tissue sampling. Current generations of video bronchoscopes are all built with a 60 cm working length. These bronchoscopes are suitable for accessing distal airways to place the guide wire over which a delivery channel or an energy delivery catheter can be exchanged.

Navigation bronchoscopy (NB) consists of two primary phases: planning and navigation. In the planning phase previously acquired CT scans are utilized to mark and plan pathways to targets within the lung. In the navigation phase, these previously planned targets and pathways are displayed and can be utilized for navigation and access deep within the lung. Upon arriving at the target NB enables multiple applications all within the same procedure. CT scans of the patient's chest are loaded into proprietary software that reconstructs the patient's airways in multiple 3D images. The physician utilizes these images to mark target locations and plan pathways to these target locations within the lungs. Using the planned pathway created in the planning phase and real-time guidance, the physician navigates a sensed probe and extended working channel to the desired target location(s). Once at the desired location, the physician locks the extended working channel in place and the sensed probe is removed. The extended working channel provides access to the target nodule for bronchoscopic tools or catheters.

Collapsing a Portion of Targeted Lung Tissue

The lungs are divided into five lobes as shown in FIG. 1, including the right upper lobe, right middle lobe, right lower lobe, left upper lobe, and left lower lobe. The lobes are in turn divided into segments. Each lobe and segment is generally autonomous and receives its own bronchus and pulmonary artery branch. If an airway supplying a lobe or a segment is occluded with a one-way valve or occluded with an obturator and the air is sucked out it will collapse or reduce in volume leading to local tissue compression under the pressure exerted by the rest of the lung. Unlike most tissues in the body susceptible to tumors, lung tissue is intrinsically highly compliant, compressible and ultimately collapsible. Atelectasis refers to a complete or partial collapse of a lung, lobe or portion of a lung. When an airway is blocked, there is no, or reduced, negative pressure delivered to that target portion of the lung. Therefore, the neighboring portions or segments compress it and remove the entrapped air. Alternatively, or additionally, vacuum suction may be applied through a lumen in the blocking device (e.g. balloon). The vacuum can be used to further remove the air out of the targeted lung portion. As a result, further or more efficient collapsing may be achieved. For the purposes of this disclosure the phrase "collapsing a portion of lung" refers to compressing or reducing or shrinking the portion of lung and complete collapse is not necessarily the intention. Without more air, the sac shrinks. It is understood that in some cases collateral ventilation may re-inflate the collapsed segment but it is expected that tissue shrinking from building up heat and continuous suction can overcome, at least partially, the re-inflation of the target area. Balloons may be used to seal the entry to a target airway when inflated. A lumen through the balloon may be used to provide the additional vacuum suction.

Lung compliance is an important characteristic of the lung. Different pathologies affect compliance. Particularly relevant to cancer ablation are the observations that: fibrosis is associated with a decrease in pulmonary compliance; emphysema/COPD may be associated with an increase in pulmonary compliance due to the loss of alveolar and elastic tissue; and pulmonary surfactant increases compliance by decreasing the surface tension of water. The internal surface of the alveolus is covered with a thin coat of fluid. The water in this fluid has a high surface tension, and provides a force that could collapse the alveolus. The presence of surfactant in this fluid breaks up the surface tension of water, making it less likely that the alveolus can collapse inward. If the alveolus were to collapse, a substantial force would be required to open it, meaning that compliance would decrease drastically. Atelectasis, clinically defined as collapse of the lung area visible on X-ray, is generally not desired. However, localized lung collapse can be beneficial in the treatment of emphysema and, as the authors propose, targeted lung cancer ablation. Advantages to collapsing or volume reducing the targeted lung portion that contains a targeted tumor during tumor ablation may include the following: electrodes positioned in airways surrounding the tumor may be drawn closer to the tumor, thereby improving concentration of ablative energy or increasing efficacy of ablating the tumor; air will be removed from the collapsed, or shrunk lung tissue supplied by the airway making the delivery of ablative energy and the thermal propagation more efficient; collapse of the segment may lead to hypoxia that provoke regional hypoxic pulmonary vasoconstriction and ischemia of the lung segment which reduces metabolic cooling and improves efficient utilization of the thermal energy; the spread of irrigation fluid, such as hypertonic saline, may be confined to the targeted area, thereby providing virtual-electrode ablation outcomes mostly to the target region. This, in turn, increases the safety and reduces the ineffectiveness of energy delivery which may be caused by evaporation of irrigation fluid (caused by overheating) or by its inadvertent spread to neighboring tissues; and electrode contact with tissue may be more consistent or have greater surface area of contact. Furthermore, ablative energy such as radiofrequency electrical energy may be delivered by a computer-controlled ablation console and collapsing the lung portion may improve temperature-controlled ablation performance by increasing contact stability and pressure between the tissue and electrode(s). For example, in a collapsed or shrunk airway, temperature sensor(s) positioned in or on the electrode(s) may provide more accurate temperature feedback to the computer-controlled ablation console used to control the energy delivery parameters such as RF power, RF power ramp up slope, or duration, while increased contact stability and pressure may allow increased stability of thermal and electrical conduction allowing the temperature sensor(s) to have a more accurate representation of temperature of the tissue around the electrode. Consequently, the ablative energy delivered to the targeted lung tissue and tumor may be optimized and the temperature of the targeted tissue may be heated to an intended temperature set point in an effective and safe manner.

Collapsing of one lobe or a segment or other section of a lung defined by morphology of airways and air supply by airways can be impeded by collateral interlobular ventilation that is common in patients with incomplete interlobar fissures and partially damaged and destroyed lung. Alternative methods of segmental or lobar collapse can be employed by heating lung tissue or injecting chemicals, foam or hot steam into the targeted segment or the targeted lobe. For example, injection of hot steam into a contained space like lobe or segment results in collapsing the space. The nature of the lung is such that when a segment is collapsed, pressurized adjacent segments compress it and fill the volume vacated by the collapsed space. Techniques for collapsing or partially collapsing portion of the lung that has collateral air pathways using a bronchoscope and bronchoscope delivered tools are described for example in U.S. Pat. No. 7,412,977 B2. Partial lung collapse, particularly of an upper lobe, was previously proposed to imitate results of lung reduction surgery in advanced emphysema but has not been suggested to enhance thermal ablation (e.g. RF) of tumors. Techniques proposed included: occluders and valves, steam (e.g., thermal), foam, and glue injection into airways. Mechanical compression of a lung portion using springs or wire coils was proposed also. All off these methods can be envisioned as being modified and adopted for cancer therapy in any lobe or segment where the tumor was located on CT and identified as malignant.

Ultimately an entire lung can be temporarily collapsed using a technique of independent lung ventilation. Lungs are intubated and ventilated by separate endotracheal tubes with obturators of the two main bronchi. A patient that is healthy enough to tolerate it can breathe using mechanical ventilation of only one lung while the contralateral lung is being collapsed and operated on. Electrodes can be positioned prior to deflating and collapsing the lung. In this case collateral ventilation will not have much effect on the ability of the operator to collapse the lung.

Collapsing a portion of targeted lung may provide other advantages that facilitate tumor ablation by enhancing RF ablation lesion dimensions. Air in the lung's airway is a very poor thermal conductor and electrical conductor. Collapsing the airways (e.g., by occluding airflow or with other methods described herein) deflates them, which enhances the permeability of RF through the previously aerated tissue. We therefore propose collapsing of a target lung portion as of the means to facilitate improved delivery energy through electrodes combined with a device such as an endobronchial catheter. A balloon (e.g., filled with liquid or air), another space occluder, a deployable valve, injected steam, a fan, glue injection, or stent could be used to occlude the airway and collapse a specific lung portion encompassing the targeted tumor. The balloon, for example, may be used to occlude a portion of the airway and as the airway is blocked, the blood absorbs the gas inside the alveoli. Alternatively, the entrapped air may be sucked out using vacuum pressure through a lumen in the balloon. The suction may be applied for 30 s to 10 min, depending on the level of shrinkage or collapse desired. If the airway is deprived of air the alveoli shrinks. In some cases, blood, fluids and mucus may fill, at least partially, the previously aerated space, allowing the space to conduct RF energy and heat more effectively.

In addition, collapse of the segment leads to hypoxia that leads to regional hypoxic vasoconstriction of the lung. Reduced blood flow to the targeted region of the lung results in less blood velocity and metabolic cooling and more efficient utilization of the thermal energy.

A procedural method of ablating a lung tumor comprising collapsing a targeted portion of the lung with a catheter configured to occlude an airway and ablate tissue may comprise the following steps: identifying the location of a targeted tumor in a lung (e.g., using medical imaging technology such as CT); Generating a 3D navigation map by registering the medical images with navigation technology; delivering a bronchoscope through the patient's airway placing the distal end in a vicinity of the targeted lung portion optionally using 3D navigation or electromagnetic navigation assistance; taking a biopsy to confirm tumor position; lubricate the bronchoscope, occlusion-ablation catheter and endotracheal tube lumen; placing the occlusion-ablation catheter through the bronchoscope working channel; steering the catheter's distal region to the targeted site navigating (e.g. by standard, virtual or navigation bronchoscopy) the ablation electrode as close to the tumor as possible optionally comprising delivering the catheter over a guidewire; optionally confirming electrode position or contact using impedance measured from the electrode, imaging or EM navigation; optionally positioning the occlusion balloon in the airway proximal to the ablation site; inflating the occlusion balloon while visualizing with the bronchoscope's lens; optionally allowing the targeted portion of lung to collapse as air is absorbed or apply other lung collapse steps as disclosed herein (e.g., apply suction to remove air from the targeted lung portion); optionally monitoring electrical impedance of tissue (e.g., between the RF electrode(s) and a grounding pad, or between bipolar RF electrodes) wherein a stable, consistent impedance indicates the lung has collapsed making greater tissue contact with the electrode(s) (e.g., in a study conducted by the authors impedance dropped about 24% to 38% when the lung collapsed); irrigating the electrode(s) or infusing conductive fluid into the targeted lung portion; delivering computer-controlled ablation energy through the electrode(s) to the targeted tissue; optionally removing fluid remaining in the lung portion through the catheter; deflating the occlusion balloon and remove the catheter from the patient; visualizing the treated airway for signs of hemorrhage or blistering, which may be treated if required. Optionally, subsequent ablations may be made at different locations by moving the ablation electrode to the subsequent location. If previously collapsed, it may be necessary to let the lung portion inflate before moving the ablation electrode if it is difficult to relocate the electrode while the lung portion is collapsed. In some situations it may be possible to keep the lung portion deflated and optionally infused with conductive fluid while relocating the electrode(s). Optionally, fiduciary markers may be placed in or around the tumor to later determine if the tumor was successfully ablated using CT.

Infusion of Conductive Fluid Into the Targeted Lung Portion

Figure 4:
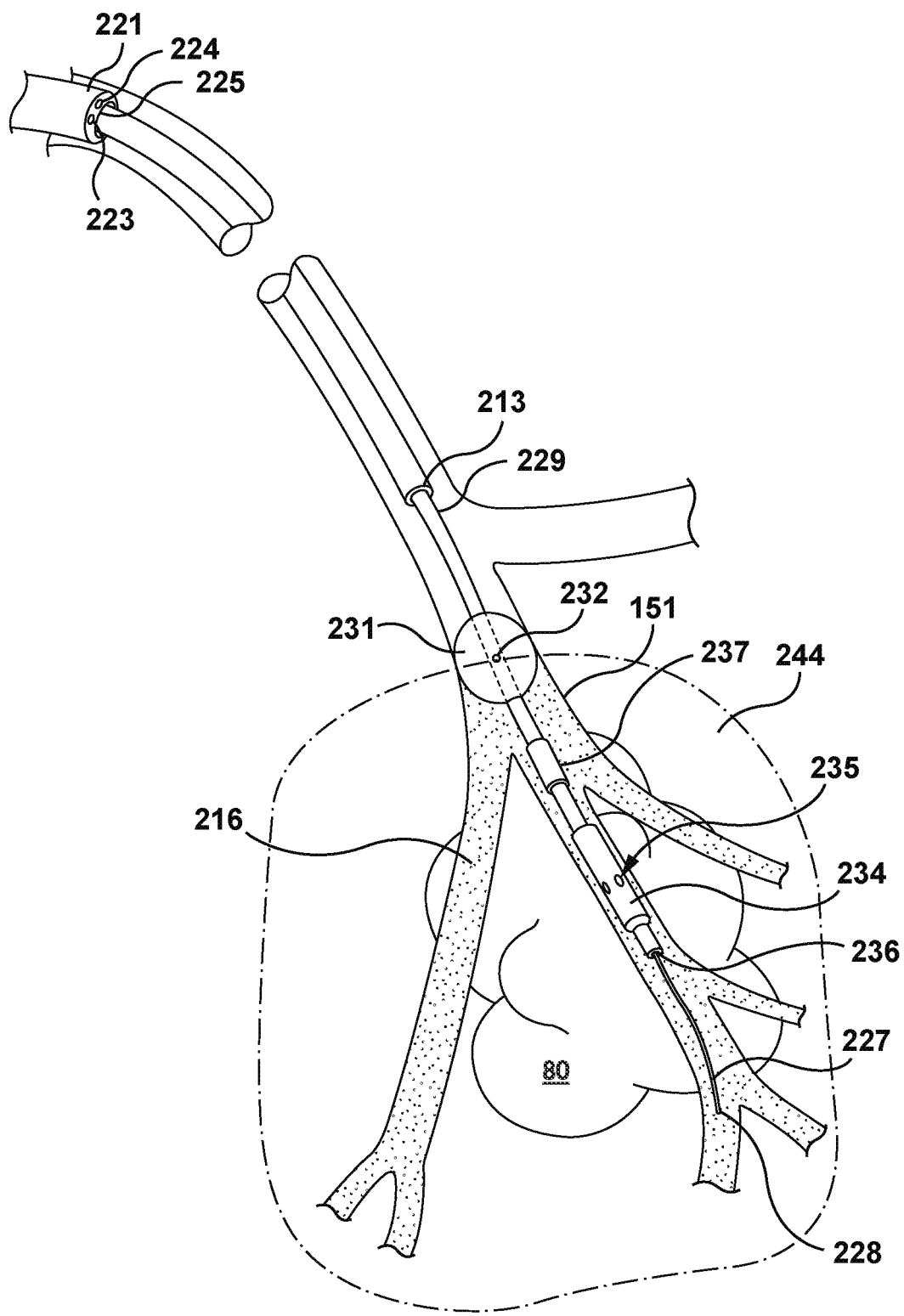
FIG. 4 is a schematic illustration of the device of FIG. 3 in situ.

In embodiments with or without collapsing (e.g., reducing or compressing) a targeted portion of a lung and injecting conductive fluid to enhance RF ablation, the injection of conductive fluid may be a volume infusion of hypertonic saline (e.g., hypertonic saline having concentrations in a range of 5% to 20%) to enhance endobronchial lung tumor ablation by creating a deeper and wider ablation (e.g., ablations greater than or equal to 1.5 cm in diameter). Other conductive fluids may be used. Optionally, a conductive fluid may have a high viscosity or may be injected in a low viscosity state to a target region and transition to a higher viscosity state in the targeted region of the body. For example, ionic salts such as NaCl or others may be mixed with a reverse phase transition polymer and water, which may transition to higher viscosity when transitioned from below body temperature to body temperature. The polymer with appropriate characteristics may be one such as a block-co-polymer PLGA-PEG-PLGA consisting of polyethylene glycol, which is covalently esterified by an FDA-approved poly lactic-co-glycolic acid on both ends. Other examples of polymers may be based on polyethylene glycol, albumin, silk, wool, chitosan, alginate, pectin, DNA, cellulose, polysialic acids, dendritic polylysine, poly (lactic-co-glycolic) acid (PLGA), gellan, polysaccharides and polyaspartic acid, and combinations thereof. The mixture may be designed to preserve the high electrical conductivity of the hypertonic saline base, while adding the higher viscosity properties of the polymer. This way, better control can be asserted over the spread of the conductive fluid. The polymer may be biodegradable, biocompatible or bioabsorbable. The ionic component may include for example, $M^+X^-$ or $M^{2+}Y^{2-}$, where M belongs to alkaline or alkaline earth metal such as Li, Na, K, Rb, Cs and X represents halogens, acetate and other equivalent counter balance to $M^+$, and Y can be $X_2$ or mixed halogens, acetates, carbonate, sulfate, phosphate and other equivalent counter balance to $M^{2+}$, as well as formic acid, glycolic acid, lactic acid, propionic acid, caproic acid, oxalic acid, malic acid, citric acid, benzoic acid, uric acid and their corresponding conjugate bases. A conductive fluid may further comprise ingredients such as pharmaceutical agents to aid tissue healing or further treatment of cancerous cells, or radiopaque contrast. The volume infused may be sufficient to infuse beyond the targeted airway and into the alveoli and lung parenchyma. This is achieved by conducting the delivered ablation energy (e.g., RF or microwave) to more tissue than the surface of the electrode contacts, thus, in effect, increasing the effective electrode size (i.e. creating a virtual electrode) and creating more stable and consistent electrical contact with the tissue. A conductive fluid, such as hypertonic saline, may also make ablation energy delivery more efficient, as less power is lost in saline and more delivered to the tissue. Less power is lost into hypertonic saline compared to physiological saline because hypertonic saline has a significantly increased electrical conductivity, and therefore lower contact impedance. With less power being lost into hypertonic saline, the boiling point is less likely to be reached. Therefore, ablations produced with hypertonic saline in a collapsed lung portion tend to not show char formation and yet produce larger lesions. Injection of conductive fluid may be done with methods and devices as described herein for injection and optional concomitant retraction of fluid and optionally with collapsing of the targeted lung portion around the electrode(s). An example of a device 220 configured to occlude the targeted portion of lung to collapse the lung portion and ablate with an irrigated electrode is shown in FIG. 4 and comprises at least one electrode 234 with at least on irrigation port 235.

Animal experiments have shown a combination of infusing hypertonic saline into an airway and delivering thermal energy to the airway by way of radiofrequency has an impressive effect of killing tissue as seen on CT scans taken 2 weeks following the procedure. Some previous studies have shown that hypertonic saline could significantly attenuate tumor cell adhesion to endothelium by inhibiting adhesion molecule and laminin expression. (Shields C J 1, Winter D C, Wang J H, Andrews E, Laug W E, Redmond H P. Department of Academic Surgery, Cork University Hospital and National University of Ireland, Wilton. *Hypertonic saline impedes tumor cell-endothelial cell interaction by* reducing adhesion molecule and laminin expression. *Surgery*. 2004 July; 136(1): 76-83.) This may halt the metastatic behavior of tumor cells shed at surgery. Other researches have reported similar studies of using saline to trigger cell apoptosis. The researchers had a study of using salt to kill cancer cells. They have created a technique which can cause cancer cells to self-destruct by injecting them with salt. (Busschaert, N., Park, S., Baek, K., Choi, Y., Park, J., Howe, E., Hiscock, J., Karagiannidis, L., Marques, I., Felix, V., et al (2017). *A synthetic ion transporter that disrupts autophagy and induces apoptosis by perturbing cellular chloride concentrations. Nature Chemistry*, 9(7), 667-675.) (Ko, S., Kim, S., Share, A., Lynch, V., Park, J., Namkung, W., Van Rossom, W., Busschaert, N., Gale, P., et al (2014). *Synthetic ion transporters can induce apoptosis by facilitating chloride anion transport into cells. Nature Chemistry*, 6(10), 885-892.) Unfortunately, when a cell becomes cancerous, it changes the way it transports ions across its cell membrane in a way that blocks apoptosis. However, it should be expected that increasing temperature can increase diffusivity of hypertonic saline (HTS) and thus the ability to transport HTS into the cells, and it could be a highly potential direction that the infusing of heated HTS or other salines may have beneficial effect of killing tumor cells.

Hot hypertonic saline (HTS) has better performances in the osmosis or diffusion to transport HTS with respect to cells, and can increase promotion of cell dehydration. The increased extra-cellular salinity results in loss of water content from within neighboring cells. As a consequence, the hot HTS bolsters the cell desiccation effects produced by the delivery of RF energy. Comparatively, a study done with a standard, off-the-shelf ablation catheter (ThermoCool) powered at 50 W and irrigated with room-temperature saline, at high irrigation rates (30 ml/min), resulted in much less cell death. The HTS with a concentration above 5%, for example 10%, can me infused to the target space and then be heated up to a certain temperature, for example a range of 75° C. to 105° C., by the electrodes located on the distal area of the catheter. Alternatively, the sequestered portion of the lung can be irrigated with heated HTS from the irrigation port on the catheter directly. The sequestered portion can be exposed to heat and HTS for a duration of at least 2 minutes, or for a duration in a range of 1 to 30 minutes accordingly, after which the HTS and the local area can be cooled down by shutting down the electrodes, irrigating or replacing with room temperature saline, or evacuated from the irrigation port directly. The procedure can be repeated until desired ablation results are achieved. It should be expected that increasing temperature can increase diffusivity of HTS and thus the ability to transport HTS into the cells, and it could be a highly potential direction that the infusing of heated HTS or other salines may have beneficial effect of killing tumor cells.

The composition of the conductive fluid, e.g., HTS, may be adjustable such that electrical or thermal conductivity or viscosity of the HTS may be adjusted. For example, a conductive fluid source may comprise multiple sources that may be combined to adjust properties of the conductive fluid that is injected into the target region of the lung. A software driven controller may be programmed to mix a predetermined or automatically determined ratio of the multiple sources before or during injection of the combined fluids into a natural airway of the lung at the target region to be ablated. For example, separate pumps may be activated at a controlled rate and duration to selectively take a desired amount of each of the multiple sources. The multiple fluids may be pumped to a mixing chamber prior to delivering the combined fluid through the device to the target region, or they may be concurrently or sequentially delivered directly to the target region. Automatic determination of a ratio of multiple sources may be calculated by the controller using input from sensors, for example located on the distal region of the device.

Optionally, the controller may adjust ablation energy delivery parameters (e.g., flow rate of conductive fluid, ablation energy power, set temperature, ramp rate, duration) based on varying properties of the conductive fluid such as conductivity, viscosity, temperature, or pressure. For example, adjusting at least one of the flow rate or the conductivity of the conductive fluid may include adjusting at least one of the flow rate or the conductivity to maintain the values detected by a temperature sensor within a determined temperature range, optionally wherein the determined temperature range is between 70 and 110° C., or above a certain temperature threshold, optionally wherein the temperature threshold is 80° C. In another example, a system is configured to adjust the conductivity of the conductive fluid in the range between 10 mS/cm and 450 mS/cm at a reference fluid temperature of 25° C.

For example, during a preclinical study ablation experiment 5 ml/min of hypertonic saline was infused. Over the course of a 2 minute RF delivery, 10 ml of hypertonic saline was infused. This ablation was followed by a subsequent 2 min ablation in the same spot. Hence, a total saline volume of 20 ml was infused. The resulting thermal injury area was grossly assessed at 3.1 cm×3.5 cm×3 cm, for a total volume of approximately 17 cm$^3$. Furthermore hypertonic saline is known to be toxic to cancer cells and can alternatively or additionally chemically ablate tumor cells. The permeated saline in lung parenchyma may replace the alveolar air and spread to the surrounding alveoli through Kohn's pores and Lambert's ducts. Perfused hypertonic saline could be doped with nonionic iodinated contrast agent to render it visible on computed tomography (CT). Other conductive irrigation fluids could be imagined such as aluminum sulfate. Creating a flow of the conductive fluid with the use of suction during ablation to continuously replenish irrigation sitting in the ablation zone could further facilitate tumor ablation by removing heat generated in the fluid.

Different liquids can be mixed under computer control to create controllable, programmable and predictable concentration of conductive ions. Alternatively, a non-flowing conductive fluid pooled in the targeted lung tissue could facilitate production of a lesion sufficient to ablate a targeted lung tumor. A desired ablation volume, which may be for example a function of tumor size, distance between the targeted tumor and RF electrodes, or proximity to vulnerable non-target structures, may determine if infusion of a conductive fluid is flowing or stagnant, wherein stagnant infusion may be used for smaller ablations and flowing infusion may be used for larger ablations and optionally a greater flow rate or cooling of injected liquid may be used for even larger ablations.

Conductive fluid can be infused before the start of ablation to prepare the lung for ablation and allow for the fluid to flow into the tissue. Delivering conductive fluid such as hypertonic saline may allow the ablation energy console to operate at a wider range of power levels as necessary to achieve therapeutic goals.

Figure 13:
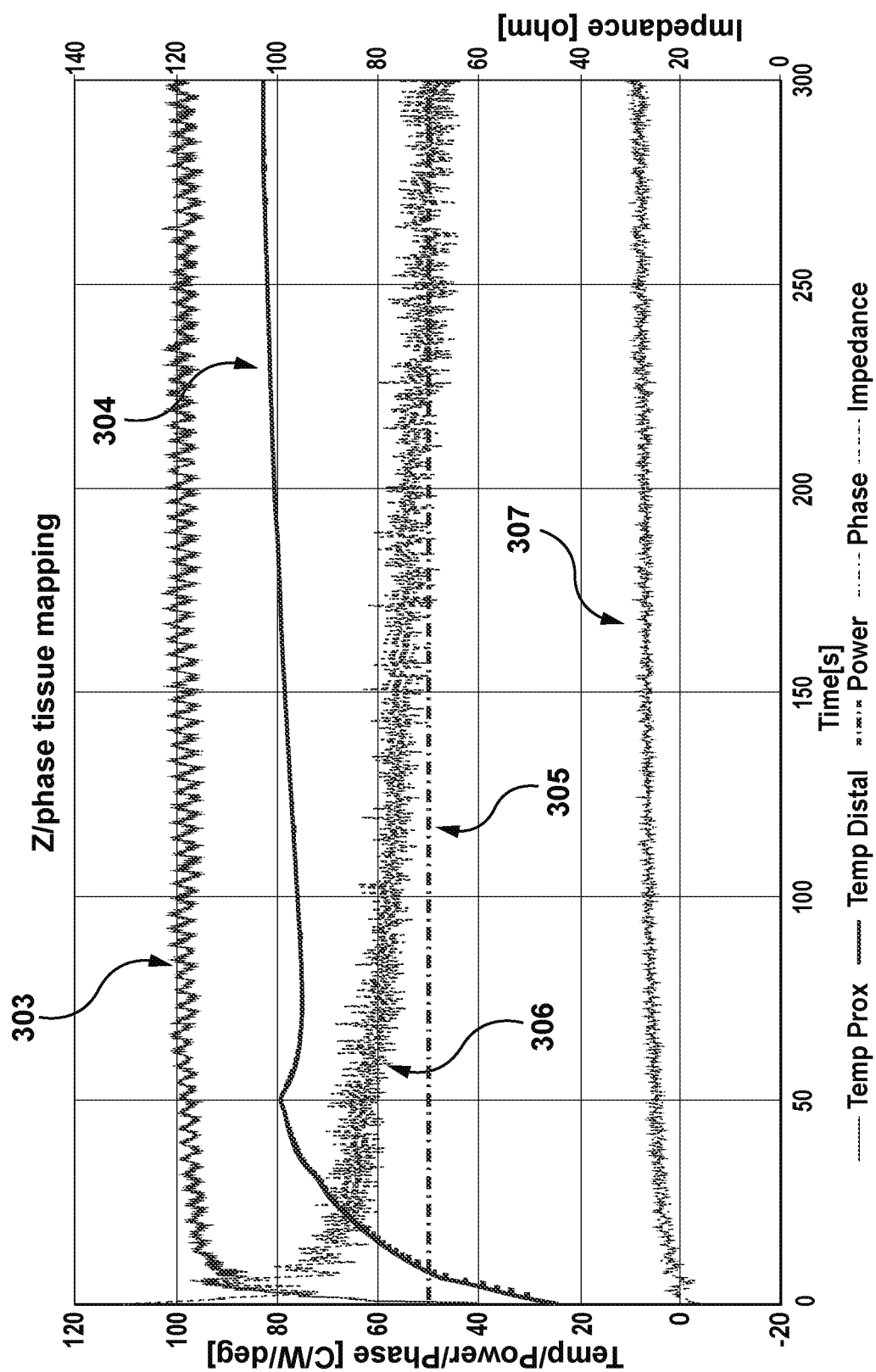
FIG. 13 is a graph of electrode temperatures, power, phase and impedance during RF delivery with hypertonic saline irrigation.

FIG. 13 illustrates an example of proximal electrode temperature 303, irrigated distal electrode temperature 304, power 305, impedance 306 and phase 307 ranges achieved by infusing hypertonic saline at a rate of 1 ml/min. The temperature may be regulated within a range above 70° C.

but below 100° C., although it may fluctuate outside such range for limited periods of time.

Optionally, a conductive fluid may be injected through a needle catheter positioned in an airway into the parenchyma or tumor, which may delivery the conductive fluid to the target site more effectively or more selectively. The needle may further comprise an RF electrode with an associated temperature and impedance sensor that may be used to deliver RF energy directly to the parenchyma near the tumor or inside the tumor.

Optionally, the conductive fluid such as hypertonic saline solution infusion may be titrated to adjust the size of ablation. Titration may be done by adjusting the saline concentration, the volume of hypertonic saline infused, or by adjusting the position of the occluding structure to block off a different size of lung portion. A higher saline concentration is more electrically conductive and may generate a larger lesion. A greater volume of infused saline may spread to a greater volume of tissue creating a larger lesion. A larger portion of lung that is occluded may accept a larger amount of infused hypertonic saline, which may result in a larger lesion. RF delivery parameters may be adjusted in accordance with hypertonic saline titration. For example, salinity of irrigation fluid may be increased in response to undesired fluctuations in impedance values.

Embodiment #1 (Cylindrical Ablation Electrode)

Figure 3:
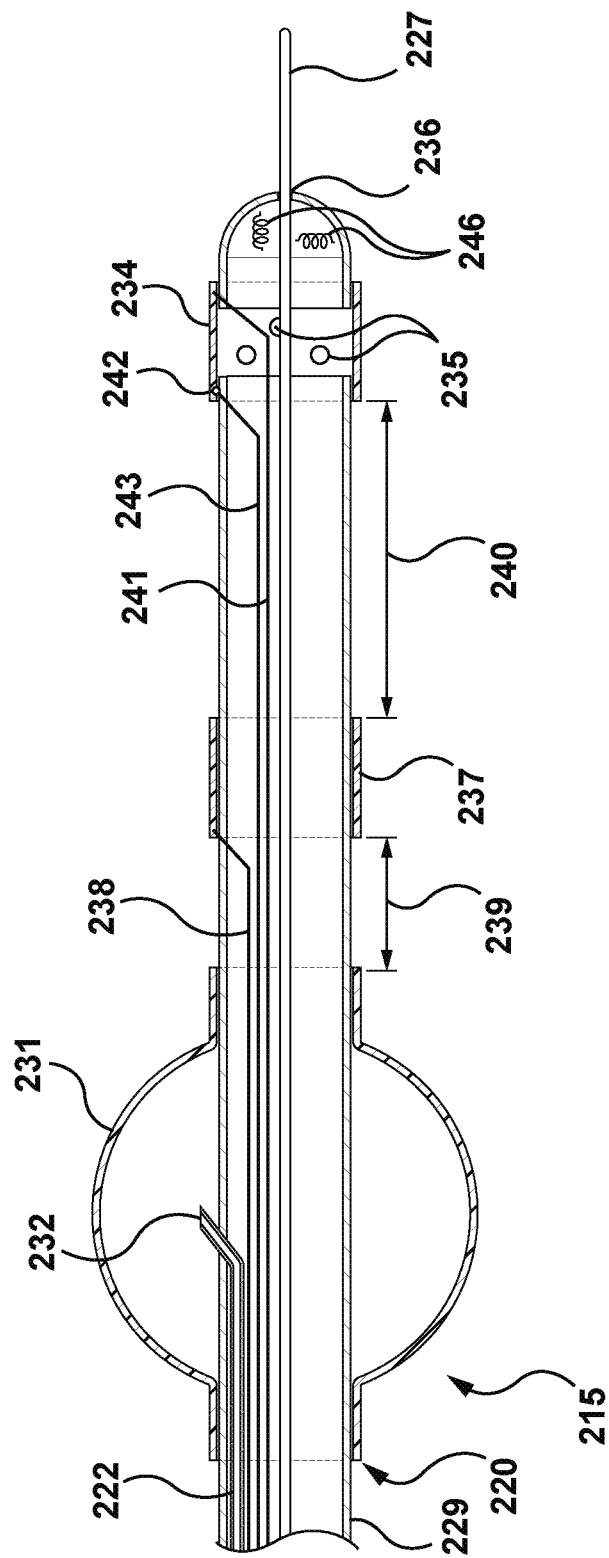
FIG. 3 is a schematic illustration of a distal region of an ablation device, constructed with one occluding balloon proximal to the electrodes.

An example of a device 220 configured to be delivered through a working channel, occlude a targeted portion of lung to collapse the lung portion, collapse the targeted portion of lung, infuse conductive solution into the targeted portion of lung, monitor tissue properties, and ablate a tumor is shown in FIG. 3. The device of FIG. 3 is shown in situ in FIG. 4.

The device 220 has an elongated shaft 229 having a proximal region intended to remain outside the patient's body and a distal region 215 intended to be delivered through a working channel to a target region of a lung proximal to a targeted lung tumor. The distal region 215 is configured to be delivered through a working channel (e.g., working channel 225 of a bronchoscope 221 or a lumen of a sheath 213 that may be delivered through the working channel of a bronchoscope). In its delivery state the device has a maximum diameter smaller than the inner diameter of the working channel through which it is delivered (e.g., less than or equal to 2 mm, less than or equal to 1.5 mm). Optionally, the device 220 may have a guidewire lumen 236 (e.g., a polyimide tube with an inner diameter of 0.015" running through a lumen in the shaft 229) so the device may be delivered over a guidewire 227. The Shaft 229 may be made for example from Pebax 720 with an outer diameter of 0.055". The shaft may be a flexible shaft capable of turning such that a bend in the shaft has a radius of curvature of less than 2.5 cm, and wherein the flexible shaft has a diameter no greater than 2 mm and a length of at least 60 cm.

The device 220 is configured to temporarily at least partially occlude an airway that feeds the targeted lung portion. As shown in FIGS. 3 and 4 the device 220 has an occlusion element such as an inflatable balloon or obturator 231. The elongated shaft 229 comprises a lumen 222 (e.g., a polyimide tube with an inner diameter of 0.015" running through a lumen in the shaft 229) with a port 232 positioned in the obturator 231 for inflating and deflating the obturator. The obturator 231 may be a balloon (e.g., compliant balloon) sized to occlude the airway or a range of airway diameters (e.g., diameters in a range of 3 mm to 10 mm). The obturator 231 may be inflated by injecting fluid (e.g., gas such as air, or liquid such as water or saline, or contrast solution) through the lumen 222 and into the obturator 231. Optionally, fluid may be injected manually with a syringe connected to a proximal region of the device 220 and fluid pressure may be contained by closing lock stop valve. The obturator may be deflated for removal by opening the lock stop valve and pulling the inflation fluid from the balloon using the syringe. Alternatively, a system for operating the device may comprise a pump to inject or remove fluid to inflate or deflate the balloon.

Alternatively, the occlusion balloon 231 may be a different form of occlusion structure such as a deployable valve, or a deployable stent with an occluding material such as PTFE.

FIG. 4 illustrates the ablation apparatus 220 shown in FIG. 3 introduced into a selected airway 151 comprising an elongated shaft 229, an obturator 231 positioned on a distal region of the shaft to occlude the airway, an air removal port 235 in fluid communication with a lumen (not shown) that is connectable at the proximal region of the device to a suction device (e.g., vacuum pump) to remove air from the airway 151 distal to the obturator 231 to collapse the targeted portion, segment or lobe of the lung. Air may be removed from the targeted lung portion by applying negative pressure (e.g., with the suction device) to the lumen that is in communication with the air removal port 235, that pulls air from the lung portion through the lumen to a proximal region of the apparatus external to the patient. As shown the air removal port 235 is the same port through which a conductive fluid (e.g., hypertonic saline) may be delivered. Alternatively, air may be removed from the targeted portion of lung by applying suction to a different lumen such as guidewire lumen 236 or an additional lumen (not shown) having an exit port on the shaft 229 distal to the obturator 231. Alternative methods of at least partially collapsing a targeted portion of lung are described herein.

Figure 9:
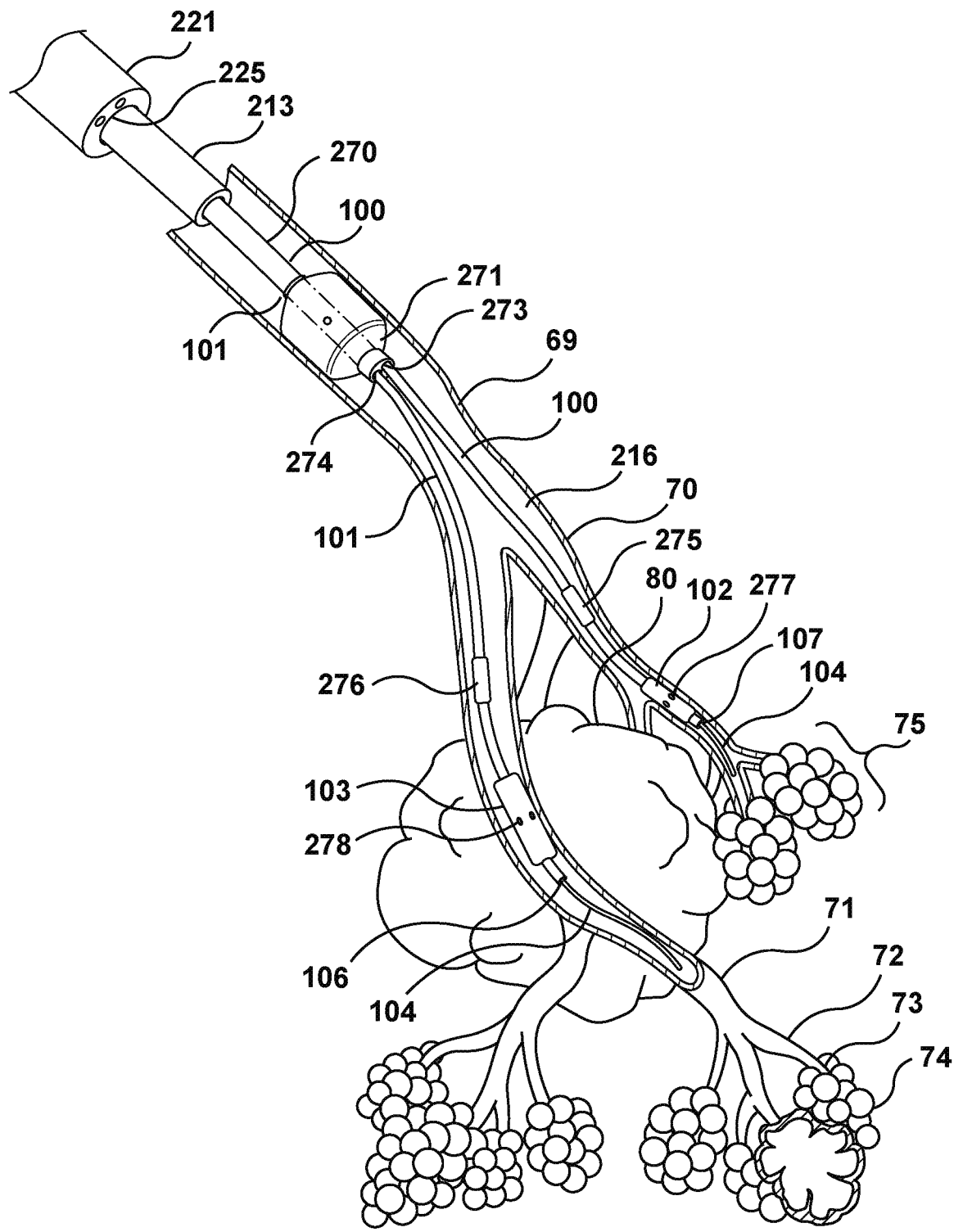
FIG. 9 is a schematic illustration of multiple catheters positioned in a patient's airways to place energy delivery electrodes at different locations associated with a targeted tumor.
Figure 12:
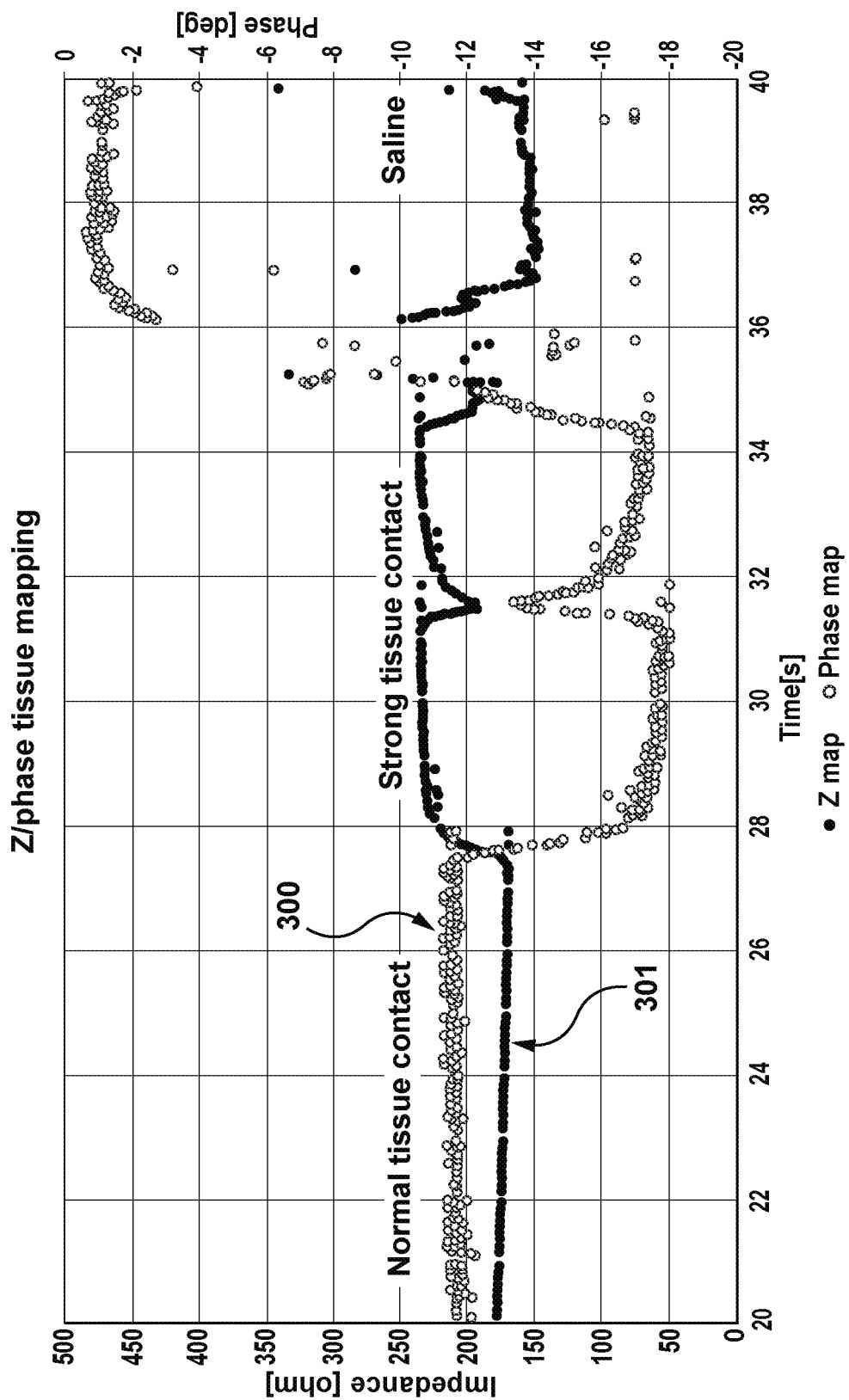
FIG. 12 is a graph of impedance and phase during periods before lung portion collapse, following lung portion collapse, and following injection of hypertonic saline during an experiment.

The device 220 shown in FIGS. 3 and 4 further comprises a distal electrode 234, (434 in FIG. 5A and 534 in FIG. 5B) positioned on the distal region 215 of the device 220 and connected to a conductor(s) 238 241, 441, 541 (e.g., copper wire 32 AWG) that runs through the shaft 229, 429 of the device to the proximal region where it is connectable to an energy delivery console. The distal electrode 234, 434 may be cylindrical in shape and have a diameter in a range of 1 to 2 mm (e.g., about 1.5 mm) and a length in a range of 4 to 7 mm (e.g., about 5 mm). An optional proximal electrode 237, 437 is positioned on the shaft 229 distal to the obturator 231, 431 (e.g., a distance 239, 439 in a range of 5 to 40 mm, about 20 mm) and proximal to the distal electrode 234, 434 (e.g., a distance 240, 440,540 in a range of 5 to 20 mm, about 10 mm). The proximal electrode 237, 437 is connected to a conductor 241238, 438, 538 (e.g., 32 AWG copper conductor) running through the shaft 229, 429, 529 to the proximal region of the catheter where it is connectable to an energy delivery console. As shown in FIG. 9, the distal 102 and proximal 103 electrodes may be used together to complete an electrical circuit used to measure or monitor electrical impedance and phase of the tissue proximal to the two electrodes. The impedance or phase may be used to assess the state of lung portion collapse during a step of collapsing the lung portion or during ablation energy delivery, or to assess degree of infusion of conductive fluid into the targeted lung portion, or to assess degree of ablation of tissue proximate the electrodes. For example, in bench tests performed by the bipolar impedance measured between a distal electrode (e.g., 234 of FIG. 3) and a proximal electrode (e.g., 237 of FIG. 3) drops about 5 to 20% (e.g. from about 400° C. to about 350° C.). Correspondingly, the phase would increase from approximately a pre-collapse range of −20° to −60° down to a post-collapse range of −10° to −30°. FIG. 12 shows representative values of impedance 300 and phase 301 at 480 kHz under various tissue contact scenarios including "normal tissue contact", "strong tissue contact" following collapse of the targeted lung portion, and "saline" after hypertonic saline was injected into the targeted airway. Additionally, when filling up the space in a collapsed airway with hypertonic saline the electrical impedance shows a steady and consistent decrease during a first portion of an RF application. The consistent and stable behavior of electrical impedance may be used to indicate to a user that the targeted airway has collapsed providing greater tissue contact.

Hypertonic saline (HTS) refers to any saline solution with a concentration of sodium chloride (NaCl) higher than physiologic (0.9%). Commonly used preparations include 2%, 3%, 5%, 7%, and 23% NaCl and are generally available in sterile bags or bottles through the hospital pharmacy. It is used in medical practice for its osmotic, rather than conductive qualities (e.g. to reduce edema).

Conductive fluid (e.g., 5 to 20% hypertonic saline) may be delivered to the targeted lung portion through irrigation ports 235 (435 in FIG. 5A, and 535 in FIG. 5B) in the electrode(s) 234 or additionally or alternatively through an infusion lumen (not shown) exiting the device 220 distal to the occlusion balloon 231 that may or may not exit through ports in an electrode. The infusion lumen runs from the irrigation ports (e.g., 235, 435, 535) through the shaft 229 to the proximal region of the device where it is connectable to a conductive fluid supply and optionally pump. Alternatively, the guidewire lumen 236, 436, 536 may be used to infuse the conductive fluid. Alternatively, or additionally in combination with collapsing a targeted portion of lung, the previously aerated space may be infused with an electrically conductive fluid such as hypertonic. Use of hypertonic saline may enhance RF delivery based on the virtual electrode effect.

While the targeted lung portion is occluded with the obturator 231, optionally collapsed, and infused with conductive liquid RF ablation energy may be delivered from an energy delivery console to the distal electrode 234. A temperature sensor 242 (442 in FIG. 5A, and 542 in FIG. 5B) (e.g., T-Type thermocouple) may be positioned on or in the distal electrode 234 and be connected to thermocouple wire 243, 443, 543 running through the shaft 229 to the proximal region of the device 220 where it is connectable to an energy delivery console. The temperature sensor 242 may be used to monitor electrode 234 temperature during energy delivery in which it is used as a parameter to control energy delivery (e.g., temperature controlled power delivery to meet a set point temperature in a range of 45° C. to 95° C., preferably between 50° C. and 80° C., or constant power controlled power delivery with a maximum temperature in a range of 45 to 95° C., preferably between 50 to 80° C., depending on specific local conditions to avoid over heating). As shown in FIG. 4 the extent of an ablation 244 is highly influenced by the infusion of conductive fluid to the targeted lung portion.

A return electrode to complete the electrical circuit may be a dispersive electrode be positioned on the patient's skin wherein the RF energy conducts through tissue between the distal electrode 234 and the dispersive electrode. Optionally or alternatively, the proximal electrode 237 may also be used to delivery ablation energy.

As shown in FIG. 4 a bronchoscope 221 having a lens 224 and light 223 is positioned in a patient's airway and a catheter 220 configured for airway occlusion and tumor ablation is delivered through the bronchoscope's working channel 225 to a targeted portion of lung 226 (e.g., a lung portion, lobe, or segment). A guidewire 227 may comprise a navigation sensor 228, or the distal end of the ablation catheter may comprise a navigation sensor 246 (see FIG. 3) (e.g., virtual bronchoscopy, electromagnetic, 3D electromagnetic, ultrasound) which may be positioned at a targeted position using a 3D navigation system and the catheter 220 may be advanced over the guidewire via guidewire lumen 236. Optionally, the catheter 220 may be telescopic wherein the distance from the obturator 231 and distal electrode is adjustable and may comprise a first elongated shaft 229 with an occlusion balloon 231 mounted to the distal region of the shaft 229 that is inflated by injecting fluid (e.g., air, sterile water, saline) through a lumen in the first shaft in fluid communication with a balloon inflation port 232 located inside the balloon. The first shaft 229 comprises a lumen 233 through which a second shaft 230 comprising at least one ablation electrode 234 may be telescopically advanced. Alternatively, an ablation electrode may be positioned on the first shaft distal to the occlusion balloon with a fixed or adjustable distance between the balloon and electrode(s) as shown in FIG. 3. A telescopic or adjustable distance between the balloon and electrode may advantageously allow placement of the electrode next to the tumor and placement of the occluding balloon at a desired position, which may depend on the geometry of the airway, the size of targeted lung portion, or the size of tumor. Optionally, the second shaft 230 may be deflectable or rotatable with respect to the first shaft 229. The ablation electrode(s) 234 may optionally comprise at least one irrigation port 235 for irrigating the electrode.

Alternatively or additionally a fiberoptic lens may be positioned on the first elongated shaft 229 distal to the occlusion structure, which may be used to visualize the airway distal to the occlusion structure. This may facilitate for example confirmation of airway shrinking, position of the electrode(s), or injury to the airway while the occlusion structure is deployed.

Optionally, if the electrode is irrigated by injecting fluid through ports 235 the fluid may be retracted by applying suction to the guidewire lumen 236 to create a flow of fluid.

Figure 5A:
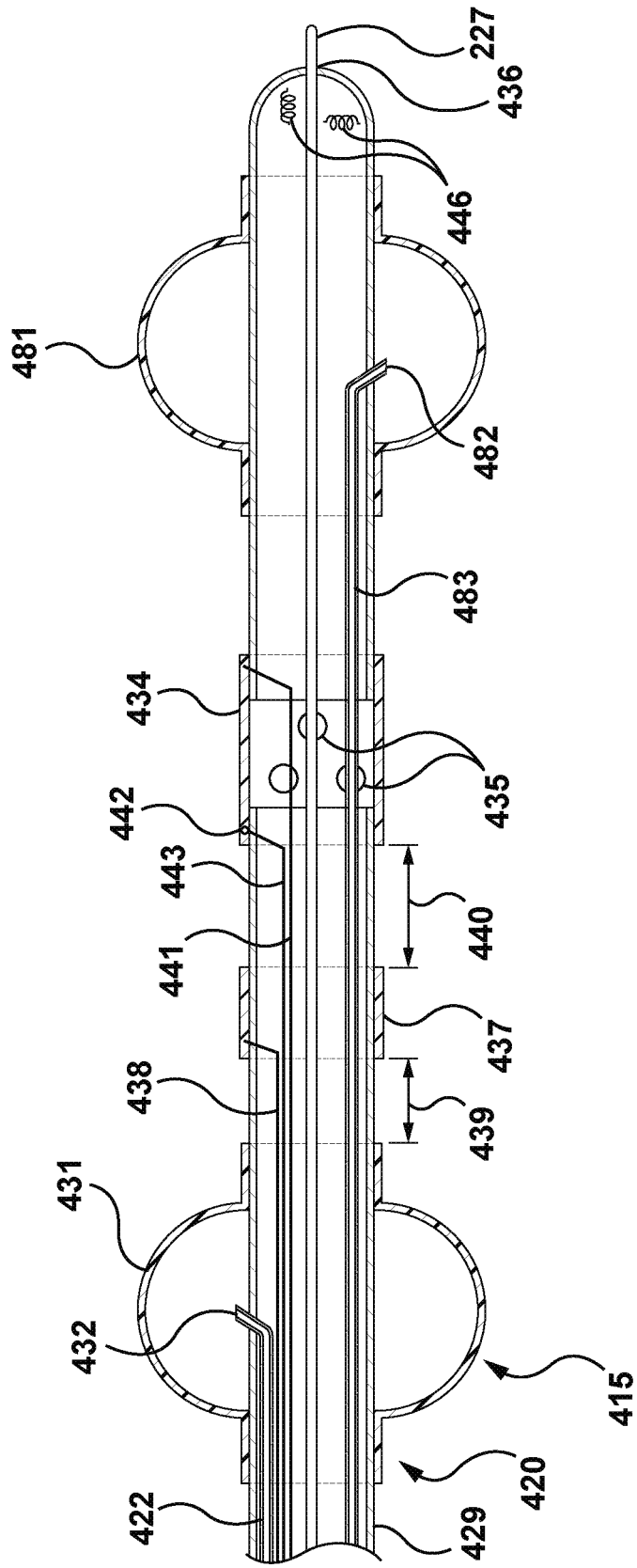
FIG. 5A is a schematic illustration of a distal region of an ablation device, constructed with two occluding balloons on the same shaft, one of which is proximal to the electrodes and the other is distal to the electrodes.
Figure 6A:
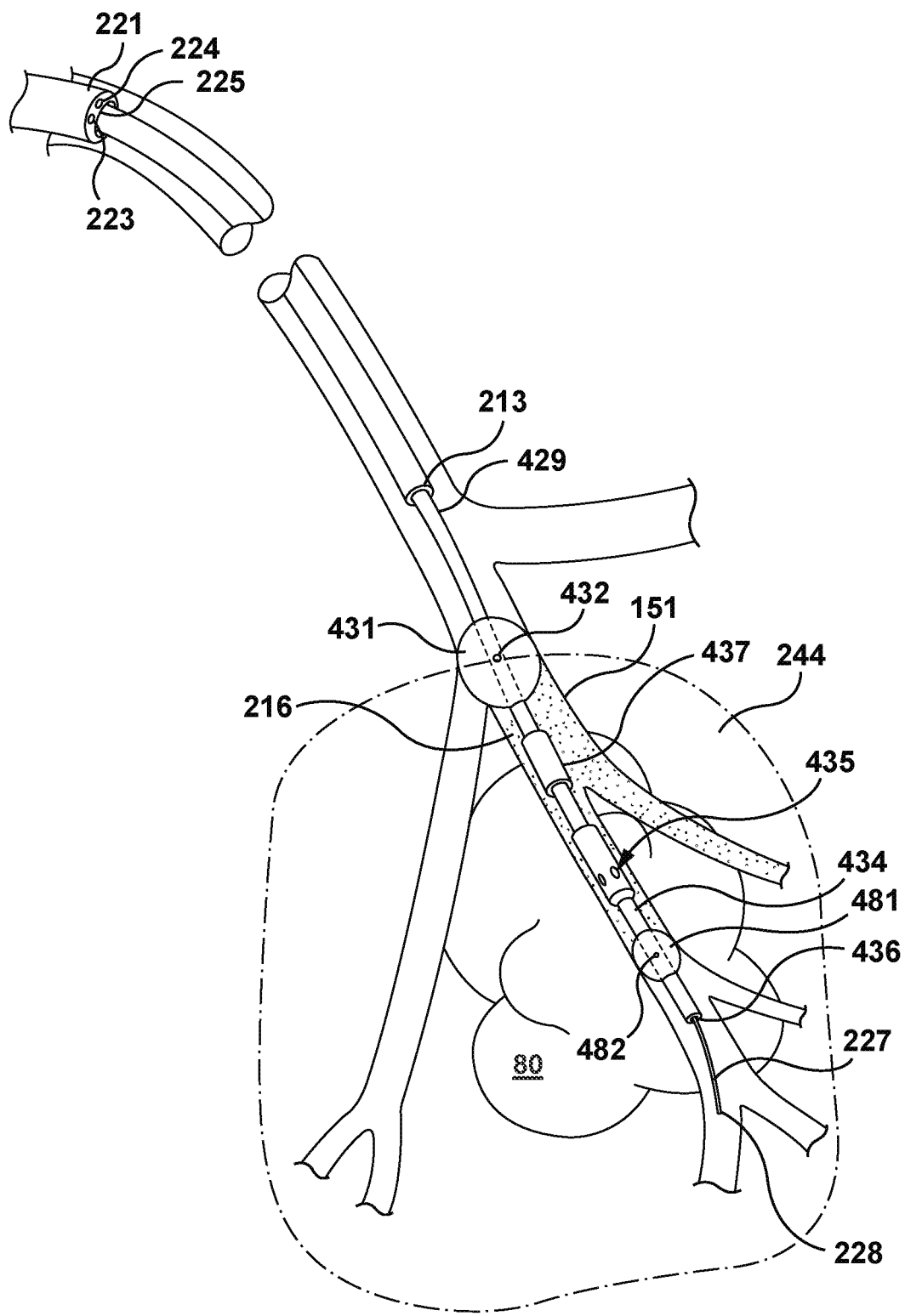
FIG. 6A is a schematic illustration of the device of FIG. 5A in situ.

Alternatively, as shown in FIGS. 5A and 6A, the device 420 can have two occlusion elements such as inflatable balloons or obturators 431, 481. One occlusion element is located proximal to the ablation electrodes, and the other is distal to the electrodes. The elongated shaft 429 comprises two lumens 422, 483 (e.g., a polyimide tube with an inner diameter of 0.015" running through a lumen in the shaft 429) with the corresponding ports 432, 482 positioned in the obturators 431, 481 for inflating and deflating the obturators. The obturator 431 or 481 may be a balloon (e.g., compliant balloon) sized to occlude the airway or a range of airway diameters (e.g., diameters in a range of 3 mm to 10 mm). The distance between the distal obturator and the proximal obturator is prefixed in this embodiment. For example, the distance between the balloons may be in a range of 20 mm to 40 mm. The obturators 431, 481 may be inflated by injecting fluid (e.g., gas such as air, or liquid such as water or saline, or contrast solution) through the lumens 422, 483 and into the corresponding obturators 431, 481. Optionally, fluid may be injected manually with a syringe connected to a proximal region of the device 420 and fluid pressure may be contained by closing lock stop valve. The obturators may be deflated for removal by opening the lock stop valve and pulling the inflation fluid from the balloon(s) using the syringe. Alternatively, a system for operating the device may comprise a pump to inject or remove fluid to inflate or deflate the balloons simultaneously or separately.

Alternatively, the occlusion balloon 431 or 481 may be a different form of occlusion structure such as a deployable valve, or a deployable stent with an occluding material such as PTFE.

FIG. 6A illustrates the ablation apparatus 420 shown in FIG. 5A introduced into a selected airway 151 comprising an elongated shaft 429, a proximal obturator 431 and a distal obturator 481 proximal and distal to the electrodes respectively (both of them are positioned on a distal region of the shaft to occlude the airway), an air removal port 435 in fluid communication with a lumen (not shown) that is connectable at the proximal region of the device to a suction device (e.g., vacuum pump) to remove air from the airway segment between the obturators 431, 481 to collapse the targeted portion, segment or lobe of the lung. Air may be removed from the targeted lung portion by applying negative pressure (e.g., with the suction device) to the lumen that is in communication with the air removal port 435, that pulls air from the lung portion through the lumen to a proximal region of the apparatus external to the patient. As shown the air removal port 435 is the same port through which a conductive fluid (e.g., hypertonic saline) may be delivered. Alternatively, air may be removed from the targeted portion of lung by applying suction to a different lumen such as guidewire lumen 436 or an additional lumen (not shown) having an exit port on the shaft 429 between the obturators 431, 481. Alternative methods of at least partially collapsing a targeted portion of lung are described herein.

Conductive fluid (e.g., 5 to 20% hypertonic saline) may be delivered to the targeted lung portion through irrigation ports 435 in the electrode 434 or additionally or alternatively through an infusion lumen (not shown) exiting the device 420 distal to the occlusion balloon 431 that may or may not exit through ports in an electrode. The infusion lumen runs from the irrigation ports (e.g., 435) through the shaft 429 to the proximal region of the device where it is connectable to a conductive fluid supply and optionally pump.

As shown in FIG. 6A a bronchoscope 221 having a lens 224 and light 223 is positioned in a patient's airway and a catheter 420 configured for airway occlusion and tumor ablation is delivered through the bronchoscope's working channel 225 to a targeted portion of lung 226 (e.g., a lung portion, lobe, or segment). A guidewire 227 may comprise a navigation sensor 228, or the distal end of the ablation catheter may comprise a navigation sensor 264, 446 (in FIG. 7 (446 in FIG. 5A and 546 in FIG. 5B) (e.g., virtual bronchoscopy, electromagnetic, 3D electromagnetic, ultrasound) which may be positioned at a targeted position using a 3D navigation system and the catheter 420 may be advanced over the guidewire via guidewire lumen 436.

Figure 5B:
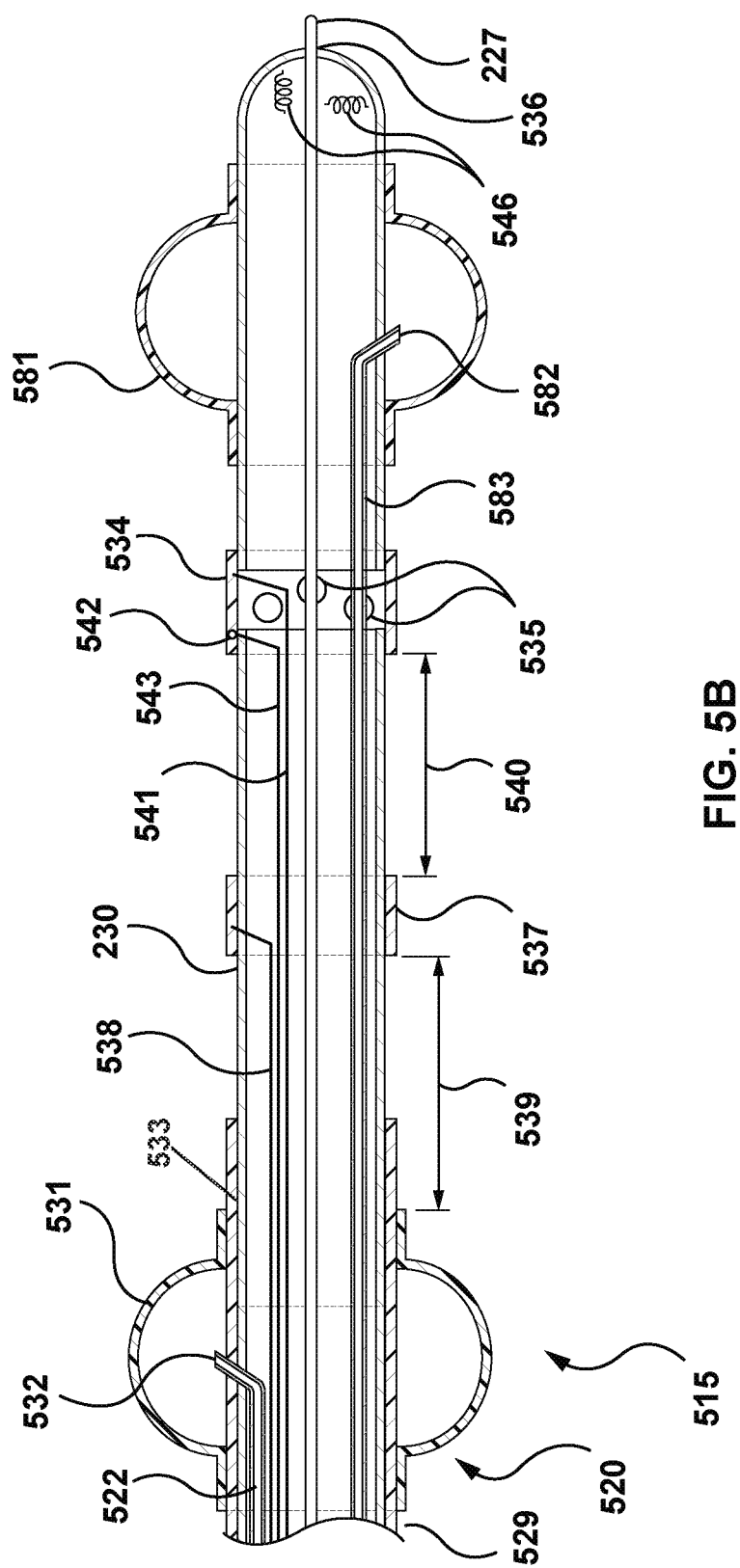
FIG. 5B is a schematic illustration of a distal region of an ablation device, constructed with two occluding balloons, one of which is proximal to the electrodes and located on a first shaft, and the other is distal to the electrodes and located on a second shaft which is extended from the first shaft.

Optionally, as shown in FIG. 5B, the device 515 includes a catheter 520 that may be telescopic wherein the distance 539 from the proximal obturator 531 and a distal proximal electrode 537 is adjustable (e.g., from a first distance in a range of 20 to 40 mm up to a second distance in a range of 30 mm to 70 mm) and may comprise a first elongated shaft 529 with a proximal occlusion balloon 531 mounted to the distal region of the shaft 529 that is inflated by injecting fluid (e.g., air, sterile water, saline) through a lumen 522 in the first shaft in fluid communication with the balloon inflation port 532 located inside the proximal balloon. The first shaft 529 comprises a lumen 533 through which a second shaft 230 comprising at least one ablation (distal) electrode 534, a proximal electrode 537, and the distal balloon 581 may together be telescopically advanced.

The second shaft 230 comprises a lumen 583 (e.g., a polyimide tube with an inner diameter of 0.015" running through a lumen in the second shaft 230) with the corresponding ports 582 positioned in the obturators 581 for inflating and deflating the obturators. The obturator 581 may be a balloon (e.g., compliant balloon) sized to occlude the airway or a range of airway diameters (e.g., diameters in a range of 3 mm to 10 mm).

Figure 6B:
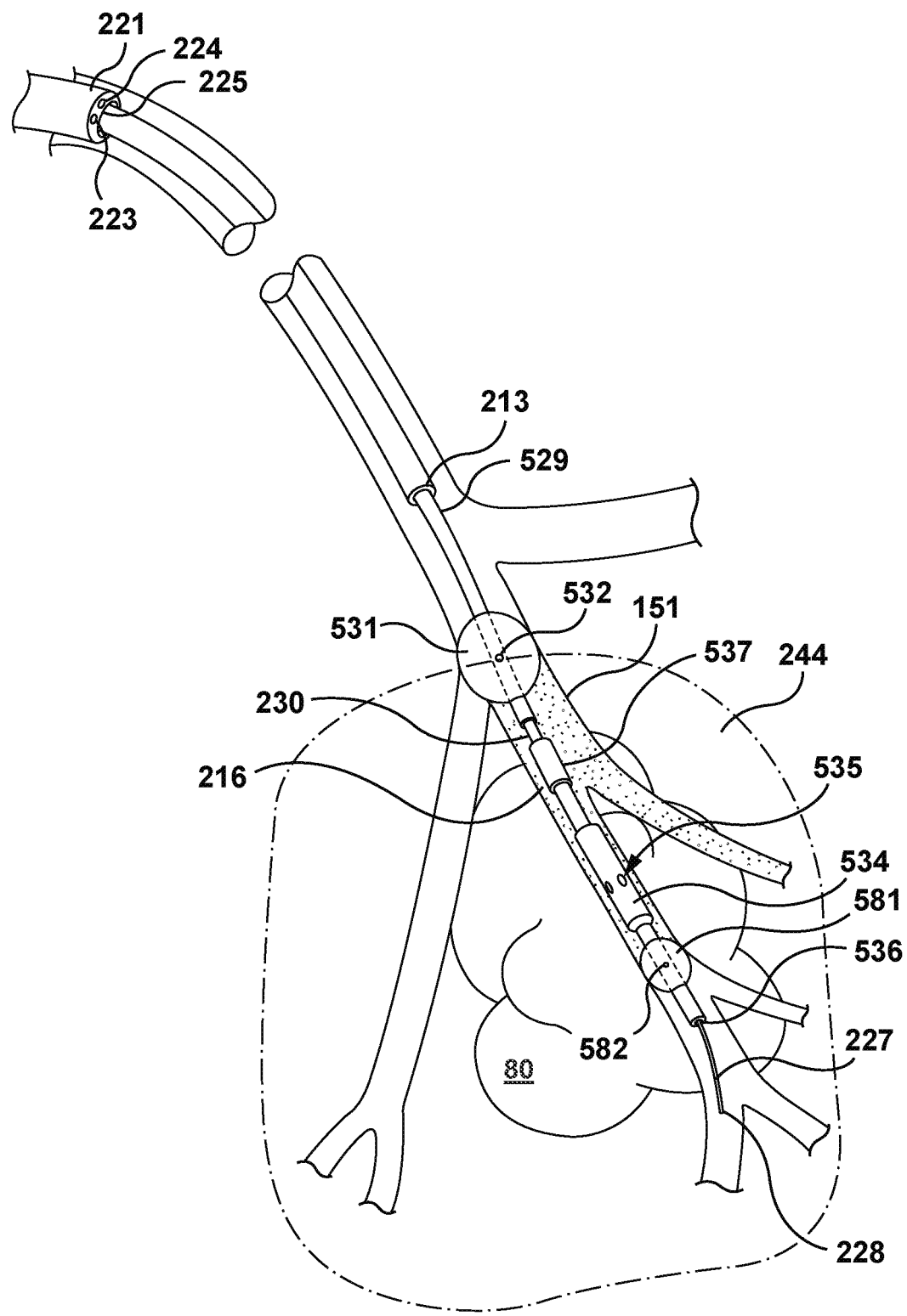
FIG. 6B is a schematic illustration of the device of FIG. 5B in situ.

FIG. 6B illustrates the ablation apparatus 520 shown in FIG. 5B introduced into a selected airway 151 comprising an elongated first shaft 529 and the second shaft 230, a proximal obturator 531 and a distal obturator 581 proximal and distal to the electrodes respectively, an air removal port 535 in fluid communication with a lumen (not shown) that is connectable at the proximal region of the device to a suction device (e.g., vacuum pump) to remove air from the airway segment between the obturators 531, 581 to collapse the targeted portion, segment or lobe of the lung. Air may be removed from the targeted lung portion by applying negative pressure (e.g., with the suction device) to the lumen that is in communication with the air removal port 535, that pulls air from the lung portion through the lumen to a proximal region of the apparatus external to the patient. As shown the air removal port 535 is the same port through which a conductive fluid (e.g., hypertonic saline) may be delivered. Alternatively, air may be removed from the targeted portion of lung by applying suction to a different lumen such as guidewire lumen 536 or an additional lumen (not shown) having an exit port on the second shaft 230 between the obturators 531, 581. Alternative methods of at least partially collapsing a targeted portion of lung are described herein.

Conductive fluid (e.g., 5 to 20% hypertonic saline) may be delivered to the targeted lung portion through irrigation ports 535 in the electrode 534 or additionally or alternatively through an infusion lumen (not shown) exiting the device 520 distal to the occlusion balloon 531 that may or may not exit through ports in an electrode. The infusion lumen runs from the irrigation ports (e.g., 535) through the second shaft 230 to the proximal region of the device where it is connectable to a conductive fluid supply and optionally pump.

A telescopic or adjustable distance between the proximal balloon and the electrode(s), or between the proximal balloon and the distal balloon, may advantageously allow placement of the electrode next to the tumor and placement of the occluding balloons at a desired position, which may depend on the geometry of the airway, the size of targeted lung portion, or the size of tumor. Especially, the adjustable distance between the proximal obturator and the distal obturator allows a more specific segment of an airway to be isolated, so any risk or unwanted influence related to the operations, such as air evacuation, fluid infusion or ablation, will be significantly reduced or minimized. Optionally, the second shaft 230 may be deflectable or rotatable with respect to the first shaft 529. The ablation electrode(s) 534 may optionally comprise at least one irrigation port 535 for irrigating the electrode.

The dual obturator structure may provide some further advantages:
  Reduced influence from collateral ventilation. Collateral ventilation is a common physiological function of a lung. During collateral ventilation, air is able to travel between lobes, bronchioles or alveolus through inter-bronchiolar passages in a lung. Although the collateral ventilation air flow is minor compared to normal respiration, it can still have effects on sufficient local air evacuation or fluid infusion. The dual obturator structure is able to provide a more sequestered space in the targeted airway. In this isolated airway segment, the influence from collateral ventilation may be minimized.

More focused therapy to the local area. In the isolated airway segment, air evacuation and conductive fluid infusion can be applied to this specific position, and the ablation energy can be more focused on this position. The obturators may also act as object blockers or energy sealants, which can reduce any air, fluid or energy diffusion effect and can save energy as well.

Reduce the risk of generating unwanted damage to pleural tissue. The dual obturator structure can provide additional fixing points to further stabilized the ablation catheter. Especially, the distal section of the ablation catheter, which comprises the ablation electrode, ablation needle or guide wire tip, is free to deform or tilt within the original strength limit of the catheter. Any accidental movement of the catheter distal section, for example, shaft 429, 529 elongation and distal tip migration due to uneven passive force during air evacuation or fluid infusion, is possible to generate unwanted damage (e.g. piercing, friction or granulation, tissue deformation) to the pleural tissue, effecting the ablation results and causing additional treatments or remedies. Furthermore, it may be desired to avoid delivering hypertonic saline or heat to pleurae or to lung parenchyma immediately next to the pleurae. A distal occlusion balloon may reduce the risk of injuring the pleurae via thermal energy or dehydration from hypertonic saline by holding the infused hypertonic saline a safe distance away from the pleurae. For example, a distal occlusion balloon may have a length of at least 10 mm, which is expected to be a safe distance from the pleurae. If the distal end of the device is inserted all the way to a distal end of an airway which may be within 10 mm of a pleura and a distal occlusion balloon is inflated, the infusion of hypertonic saline and delivery of heat may be expected to remain a safe distance from the pleura.

Using the above described ablation catheters, a method may be performed of ablating lung tumor cells by sequestering a target portion of lung proximate the tumor cells, delivering hypertonic saline (HTS) to the sequestered portion of lung, and applying heat to the sequestered portion of lung. The HTS may have a sodium (NaCl) concentration of at least 5% (w/v).

The HTS may be heated in a target region of the lung to a range of 75 to 105 degrees Celsius. The heat may be applied by delivering radiofrequency (RF) electrical current from an RF electrode on the catheter to the HTS liquid injected into a natural airway of the lung that is near the lung tumor. The target region of lung may be exposed to heat and HTS for a duration of at least 2 min, or a period in a range of one to 30 minutes.

The application of RF energy into the liquid effectively uses the liquid as a virtual electrode to delivery energy to ablate tumor cells. The HTS solutions conducts the RF energy to the lung tissue which causes the tissue to heat. Also some of the RF energy heats the liquid such that the heated liquid can ablate tumor cells.

The target portion of lung is sequestered by inflating a first occluding balloon in a natural airway, wherein the balloon is proximal to the target portion of lung. Further, a second (distal) occluding balloon in the airway distal to ablation electrode may also be used to occlude the airway. The one or both balloons occlude the natural airway form a portion of the airway in which the HTS solution is injected and suppress flow of the liquid outside of that portion of the airway.

Alternatively or additionally a fiberoptic lens may be positioned on the first elongated shaft 529 distal to the proximal occlusion structure and another lens may be positioned on the second shaft 230 distal to the distal occlusion structure, which may be used to visualize the airway distal to the selected occlusion structure(s). This may also facilitate, for example, confirmation of airway shrinking, position of the electrode(s), or injury to the airway while the occlusion structure is deployed.

Alternatively or additionally, a lung portion may be collapsed by creating a limited, controlled pneumothorax by placing a needle in the pleural space (e.g., in a pleural recess), which can facilitate collapsing the targeted lung portion. Thoracentesis (a.k.a. pleural tap) is a known procedure to remove fluid or air from around the lungs in which a needle is inserted through the chest wall into the pleural space. This may be done to alter the pressure differential between the pleural space and lung portion allowing it to collapse more easily. Optionally, a dispersive return electrode may be inserted through the pleural tap and positioned on the lung to direct RF current preferentially toward the return electrode. Optionally, a pleural tap may be used to deliver cold fluid such as physiological saline or sterile water to thermally protect areas from ablation, in particular when the tumor is at the periphery of the lung and there is a risk of ablating visceral pleura or organs such as the heart, esophagus, nerves, diaphragm or other important non-target tissues.

Embodiment #2 (Needle Electrode)

Figure 7:
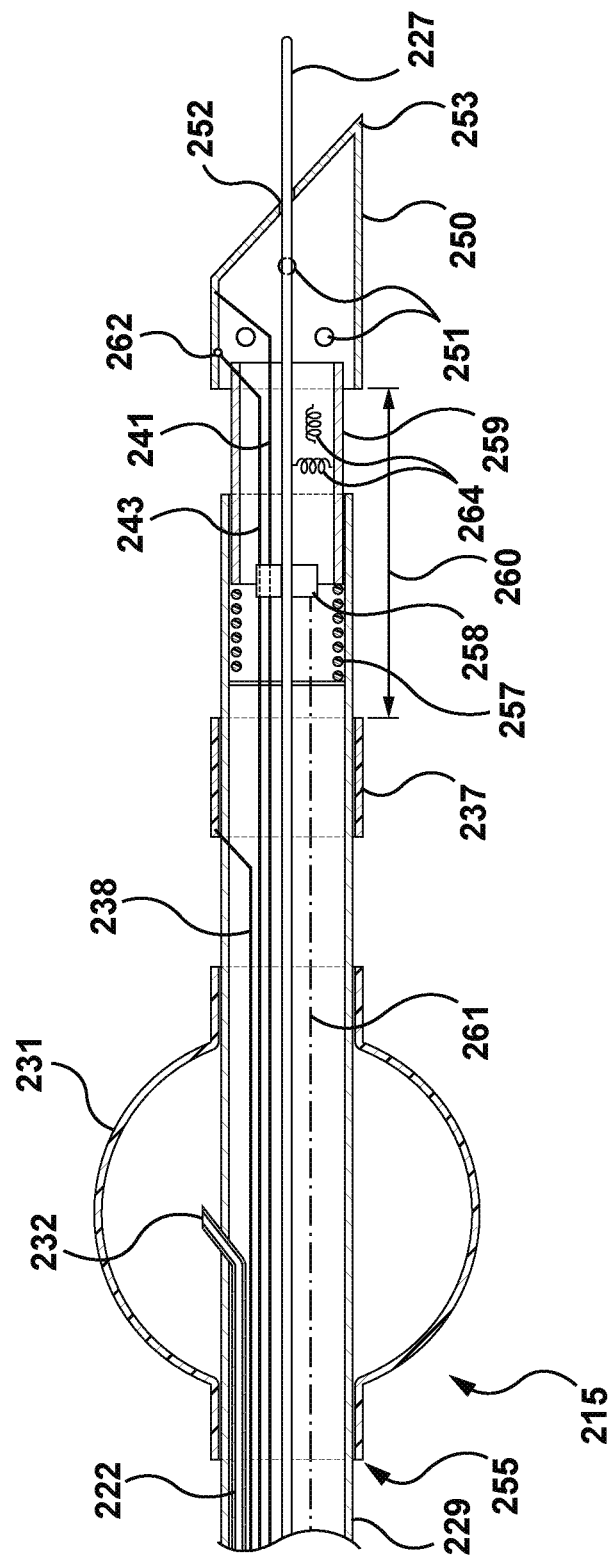
FIG. 7 is a schematic illustration of a distal region of an ablation device having a needle electrode.
Figure 8:
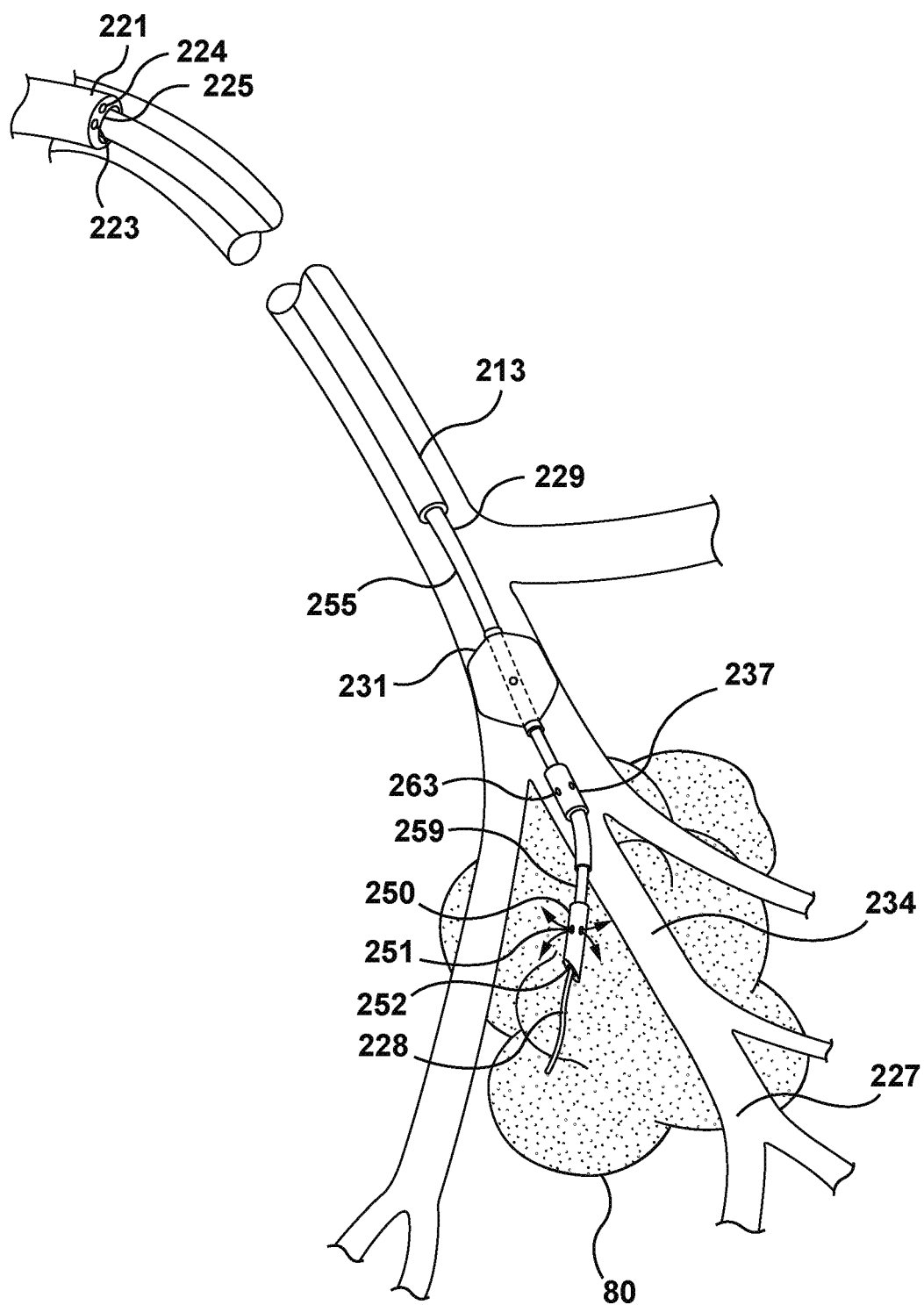
FIG. 8 is a schematic illustration of the device of FIG. 7 in situ.

Alternatively, as shown in FIGS. 7 and 8 the at least one RF electrode 234 of the embodiment shown in FIG. 3 or 4 may be at least one needle electrode 250 used to puncture through the airway wall to position an RF electrode in the targeted tumor 80 or in lung parenchyma next to the tumor. The needle electrode 250 may have irrigation ports 251 in fluid communication with an irrigation lumen passing through the shaft 229 to the proximal region of the catheter. The needle electrode 250 may have a length in a range of 5 to 10 mm (e.g., 6 to 8 mm, 7 mm), and a diameter in a range of 0.044" to 0.065" (e.g., about 0.058"). Optionally, the needle electrode may have a guide wire lumen 252 (e.g., having an inner diameter of 0.015" to 0.030") allowing the device to be delivered over a guidewire. The tip 253 of the needle electrode 250 may be sharp so it can puncture through an airway wall, for example the tip 253 may be bevel cut as shown or other sharp profile such as pencil tip. In use, conductive fluid (e.g., 20% hypertonic saline) may be injected from the irrigation ports 251 into lung parenchyma when the needle electrode 250 is positioned in the parenchyma as shown in FIG. 8.

Optionally, the device 255 may be delivered over a guidewire that is left in place in lung parenchyma or a tumor following a biopsy so the needle electrode 250 can easily be placed in the same location that the biopsy was taken.

Optionally, the distal region 256 of the device 255 having a needle electrode 250 has a spring loaded mechanism with a spring 257 and an engagement lock 258 that holds the needle electrode 250 in a first spring loaded position and when the lock 258 is released by an actuator on the proximal region of the device 255 the spring 257 pushes a shaft 259 on which the needle electrode 250 is mounted thus extending a distance 260 from a spring loaded state (e.g., 5 to 10 mm) to a deployed state (e.g., an increase of 5 to 10 mm). The momentum provided by releasing the spring-loaded mechanism may facilitate puncture of the airway wall by the needle electrode 250. The engagement lock 258 may be a mechanical mechanism such as a pivoting lever that mates with an element firmly connected to the distal shaft 259. The pivoting lever may be connected to a pull wire 261 that runs through the device shaft 229 to the proximal region of the device where it may be connected to an actuator that may be used to apply tension to the pull wire to release the lock mechanism 258.

In an alternative embodiment of a lung cancer ablation catheter capable of puncturing through an airway wall may have a RF perforation electrode on its tip (e.g., 0.5 mm diameter, 1 mm length) and the outer diameter of the shaft may taper from the RF perforation electrode diameter to the diameter of a distal ablation electrode (e.g., about 1.5 mm). An RF perforation electrode may be connectable to an energy delivery console that has an RF perforation mode. RF perforation electrodes and energy delivery profiles are known for example in the field of cardiac procedures such as septum perforation.

Optionally, the distal region of device having needle electrodes may be deflectable which may facilitate directing the sharp tip toward an airway wall in order to puncture through the wall and place the needle electrode 250 in lung parenchyma near or in a lung tumor.

Optionally, the proximal electrode 237 may be used to deliver ablative RF energy in addition to, instead of, or in conjunction with the distal electrode 250. The proximal electrode 237 may optionally have irrigation ports 263 in fluid communication with an irrigation lumen (not shown) that passes through the shaft 229 to the proximal region of the device 255 where the lumen is connectable to a conductive fluid source or pump. The irrigation ports 263 and 251 on the proximal electrode 237 and distal electrode 250 may be connected to the same irrigation lumen or separate lumens for delivery of conductive fluid. In embodiments having irrigation ports 263 on a proximal electrode 237 as well as irrigation ports 251 on a distal needle electrode 250 as shown in FIG. 8 conductive fluid may be delivered from either ports 251 or 263, preferably from both, into the lung parenchyma or tumor and/or into airways distal the obturator 231. Preferably, RF energy may be delivered to the two electrodes 237 and 250 in dual-channel monopolar RF mode. For example, each channel may have a completed circuit with a dispersive electrode on the patient's skin or in the body and channels may float with respect to one another. Alternatively, an ablation energy console may delivery RF energy to the two electrodes 250 and 237 in bipolar mode.

Embodiment #3 (Multiple Ablation Catheters)

FIG. 9 shows two catheters 100 and 101 with energy delivery electrodes 102 and 103 as an example that can be introduced separately using a flexible bronchoscope 221 and positioned with the electrodes terminating in two separate airways on two sides of the targeted tumor 80. The apparatus may include an occlusion catheter 270 that may be delivered through a working channel 225 of a bronchoscope 221 or optionally through a delivery sheath 213. The occlusion catheter 270 may comprise an obturator 271 such as a compliant balloon mounted to the shaft of the occlusion catheter 270. An inflation lumen passes through the occlusion catheter shaft and exits a port 272 within the obturator to deploy or inflate the obturator 271. The shaft of the occlusion catheter 270 may comprise two or more ablation catheter lumens 273 and 274 that exit the shaft distal to the obturator 271. Alternative forms of occlusion elements may be envisioned as disclosed herein. The catheters 100 and 101 may be delivered through the lumens 273 and 274 to the airway distal of the obturator. Lumens 273 and 274 may each have a valve that seals around delivered catheters 100 and 101 to contain low pressure or conductive fluid in the target region of the lung portion. The catheters may be delivered over a guide wire 104 via guide wire lumens 106 and 107. The electrodes may be connected to electrical conductors that pass through the catheter shafts to a proximal region of the catheter for example terminating in an electrical connector, which may be electrically connected to an RF generator for example using a connector cable. Each catheter can incorporate more than one electrode that can be energized together or separately. Optionally, each catheter may have an impedance and phase monitoring electrode 275 and 276 for monitoring tissue impedance and phase between distal electrode 103 and impedance electrode 276 or distal electrode 102 and impedance electrode 275 to assess collapse of airways, infusion of conductive fluid, tissue properties, or degree of ablation of tissue. Conductive fluid 216 may be injected into the targeted lung portion that is occluded with obturator 271 through irrigation holes 277 or 278 in electrodes 102 and 103.

The electrodes of the catheters may be positioned at a desired location in an airway by delivering the catheters 100 and 101 over a guide wire 104 laid down for example using an ultrathin bronchoscope. Catheters 100 and 101 may comprise a guidewire lumen 106 and 107 and be adapted for over-the-wire (OTW) exchange. Currently available devices may be used to navigate to desired positions in the patient's airway. For example, electromagnetic navigation bronchoscopy is a medical procedure utilizing electromagnetic technology designed to localize and guide endoscopic tools or catheters through the bronchial pathways of the lung. Virtual Bronchoscopy (VB) is a three-dimensional, computer-generated technique that produces endobronchial images from spiral CT data. Using a virtual, three-dimensional bronchial map from a recently computed tomography (CT) chest scan and disposable catheter set, physicians can navigate to a desired location within the lung to biopsy lesions, take samples from lymph nodes, insert markers to guide radiotherapy or guide brachytherapy catheters. Such existing technology may be used to plan for a procedure, diagnose a tumor with a biopsy, or place a guidewire for positioning one or more treatment catheters. After a guide wire 104 is placed in an airway near the target ablation zone (e.g., within 0 to 10 mm from the target ablation zone or within the target ablation zone) the ultrathin bronchoscope can be withdrawn with the wire left in place and an electrode catheter may be exchanged over the wire. Alternatively, electromagnetic navigation bronchoscopy may be used with similar results. Optionally, the multiple catheters may alternatively have a dual balloon structure, which is similar to the devices shown in FIG. 5A or 5B.

Multiple catheters with electrodes, or balloon elements, can be placed in the described fashion by exchanging a bronchoscope for catheter over the wire. After the tumor is thus surrounded by energy delivery elements and the bronchoscope and guide wire are removed, the proximal ends of catheters can be connected to the RF generator outside of the body. The technology subject of the present disclosure can also be used to ablate lymph nodes, should biopsy results indicate lymph node metastases.

Radiopaque markers on the guide wire or catheter can be used to position the electrodes at the precise desired location. For example, the RF electrodes may be radiopaque. Any of the ablation catheters disclosed herein may comprise a retention or anchoring mechanism at a distal region of the catheter to ensure its energy delivery element(s) stay in a desired position and avoid accidental dislodgement in particular when the patient breathes or coughs. For example, a retention or anchoring mechanism may comprise a section of the catheter that adopts a predefined non-linear shape (not shown), an inflatable balloon, spring loaded, or wire activated splines, a stent, or deployable barbs positioned on the distal region of the catheter. Size and design of the electrode catheter can be made compatible with a working channel of regular or ultra thin bronchoscopes. Multiple electric connections for energy delivery and signal transmission (temperature and impedance) are envisioned. The ablation catheters may comprise a substance delivery lumen, which may be used to deliver substances into the airway such as drugs, contrast media to visualize the anatomy using fluoroscopy, and substances that induce lung collapse. Optionally, the guide wire lumen may function as the substance delivery lumen when the guide wire is removed, which may allow the catheter's diameter to be minimized. The ablation catheters may comprise an irrigation delivery lumen used to infuse irrigation fluid into the airway surrounding the electrodes to prevent charring and impedance rise and enable bigger lesion creation. The irrigation delivery lumen may be the same lumen as the substance delivery lumen or guide wire lumen.

Figure 10A:
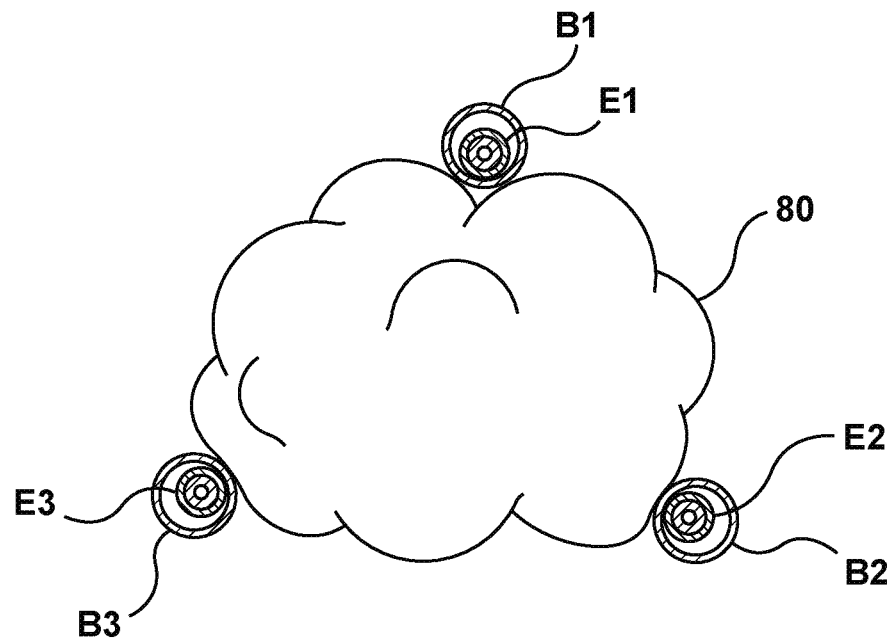
FIG. 10A is a schematic illustration of a cross section of FIG. 9.
Figure 10B:
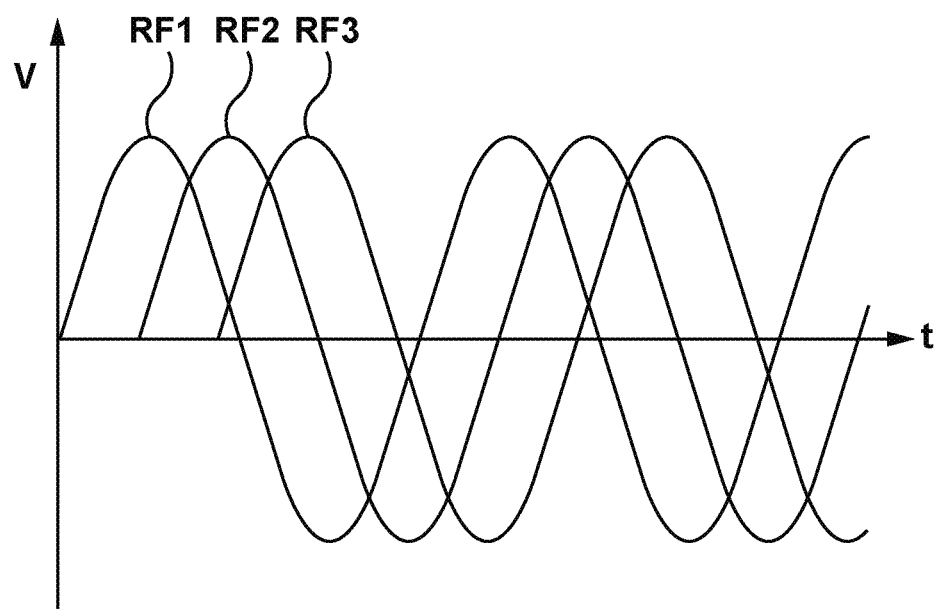
FIG. 10B is a plot of a multiphasic waveform.

As shown in FIG. 10A three RF electrodes labelled E1, E2 and E3 are positioned in three separate airways labeled B1, B2 and B3. For example, the three electrodes may be delivered on separate catheters, such as the catheter embodiment shown in FIG. 9. Multiphasic RF ablation waveforms may be used to set a rotating ablating electrical field, which delivers ablating energy to the tumor in a more localized modality. FIG. 10B illustrates a multiphasic RF waveform that may be used to ablate a targeted tumor encompassed by multiple RF electrodes, wherein RF1 is an RF signal delivered to electrode E1, RF2 is delivered to electrode E2, and RF3 is delivered to electrode E3. In this example, waveforms $RF_1$, $RF_2$ and $RF_3$ are 120° phase shifted apart. Application of such phased-shifted waveforms creates a rotating multipolar ablation field, which enhances the coverage of the tumor space and has the potential of providing more uniform lesions. In principle, phased RF ablation works similarly to bipolar ablation, except that electrical currents flow from or to a multitude of electrodes in a sequence dictated by phase differences.

Figure 10C:
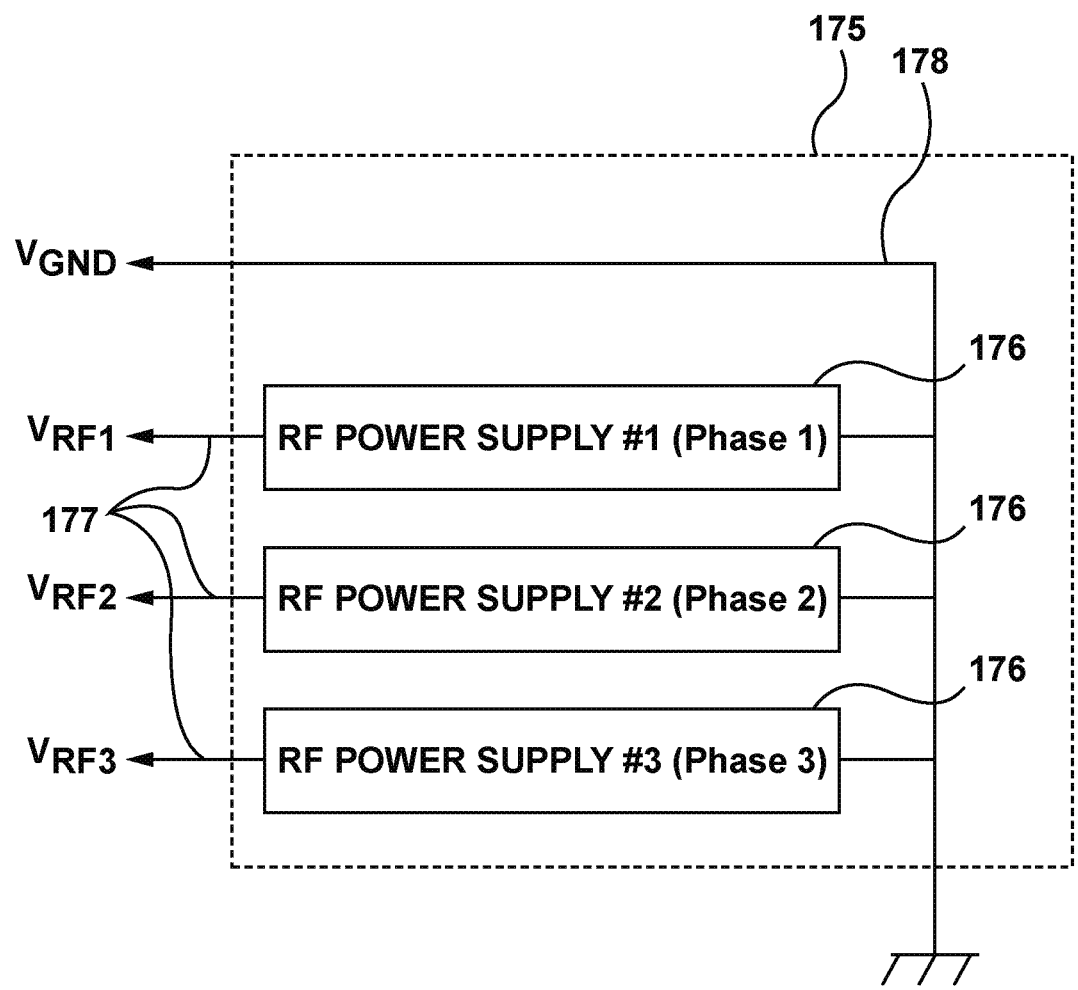
FIG. 10C is a schematic of a multiphasic RF system.
Figure 10D:
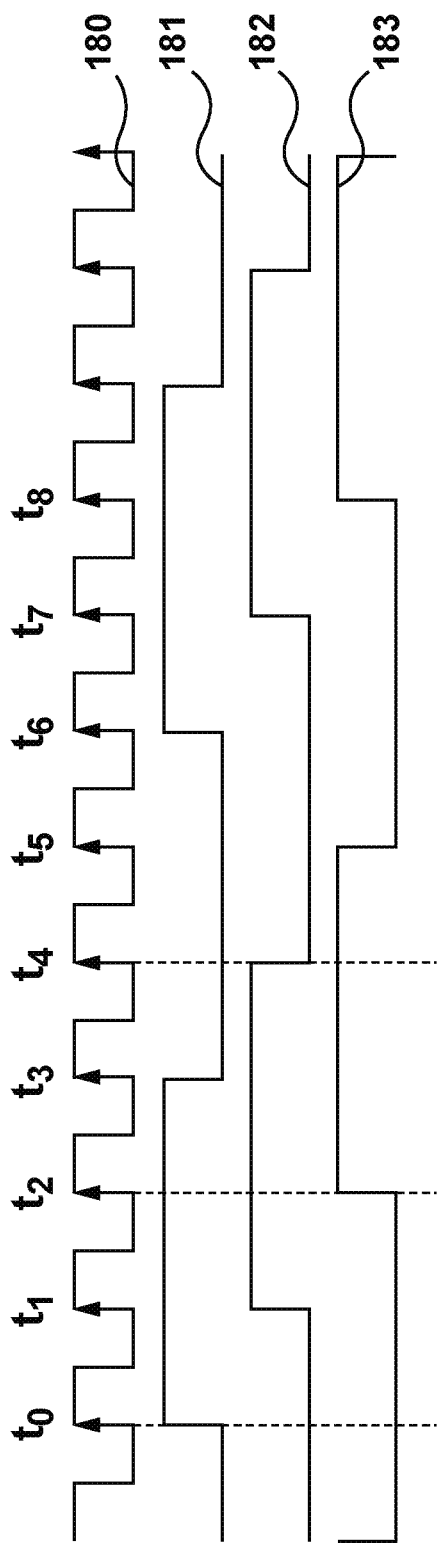
FIG. 10D is a plot of a digital clock divided to generate a multiphasic RF configuration.

Each electrode is driven by an RF source having a different phase. The RF voltage resulting between each pair of electrodes (e.g., $E_1$-$E_2$, $E_2$-$E_3$ and $E_3$-$E_1$) drives RF current to flow in more uniform heating patterns in the tumor space. Power levels range between 1 to 100 W, with durations between 30 to 600 s. Temperature sensors may be employed with an intent to control local temperature values around a user-defined target. Temperature of such targets may vary in a range of 45 to 95° C., preferably in a range of 50 to 80° C. RF generators capable of delivering phased ablation energy may have additional RF output stages. FIG. 10C shows an example of a multiphasic RF energy supply 175 where each output 177 has an independently controlled phase. The phase of RF signals at each output may be controlled by separate RF power supplies 176, or alternatively a central microcontroller, via software, or by hardware, for example by dividing a digital clock of a higher frequency, as shown in FIG. 10D. As shown in FIG. 10D a digital clock may comprise a base frequency 180 having a period (e.g., from $t_0$ to $t_1$) that is one sixth the period of frequencies 181, 182, and 183, which are delivered to the ablation electrodes and offset by one base period. Optionally, each electrode $E_1$, $E_2$, and $E_3$ (and respective RF output voltages $V_{RF1}$, $V_{RF2}$ and $V_{RF3}$) may complete an electrical circuit with a dispersive ground pad connected to ground voltage $V_{GND}$ at a terminal 178 of the RF energy supply 175. An alternative embodiment may comprise greater than three electrodes and waveforms or less than three (e.g., two electrodes and waveforms).

An example of bipolar or multipolar RF ablation parameters that an RF console delivers to multiple electrodes, or to multiple balloons, or to combinations of balloon and electrode energy elements, may comprise power in a range of 1 to 100 W for a duration of 10 to 600 seconds. Tissue impedance may be expected to be in a range of 30 to 1000 ohms and the system may terminate or reduce power delivery if a high impedance (e.g., above 1000 ohms) is detected to avoid tissue char or uncontrolled ablation due to overheating, poor electrode contact with an airway wall. After desiccated tissue is rehydrated naturally or by irrigation, energy delivery can automatically resume. Impedance monitoring may also be used during energy delivery to determine if tissue temperature has raised sufficiently for an effective tumor ablation and instigate completion of energy delivery. The parameters may be used in a multiphasic RF ablation waveform or monophasic waveform.

Optionally, an ablation energy console may delivery ablation energy to multiple RF electrodes (e.g., on a single ablation device or on separate ablation devices) in multichannel monopolar mode and independent waveforms (e.g., $V_{RF1}$, $V_{RF2}$, etc. shown in FIG. 10C) may be in-phase.

System

Figure 11:
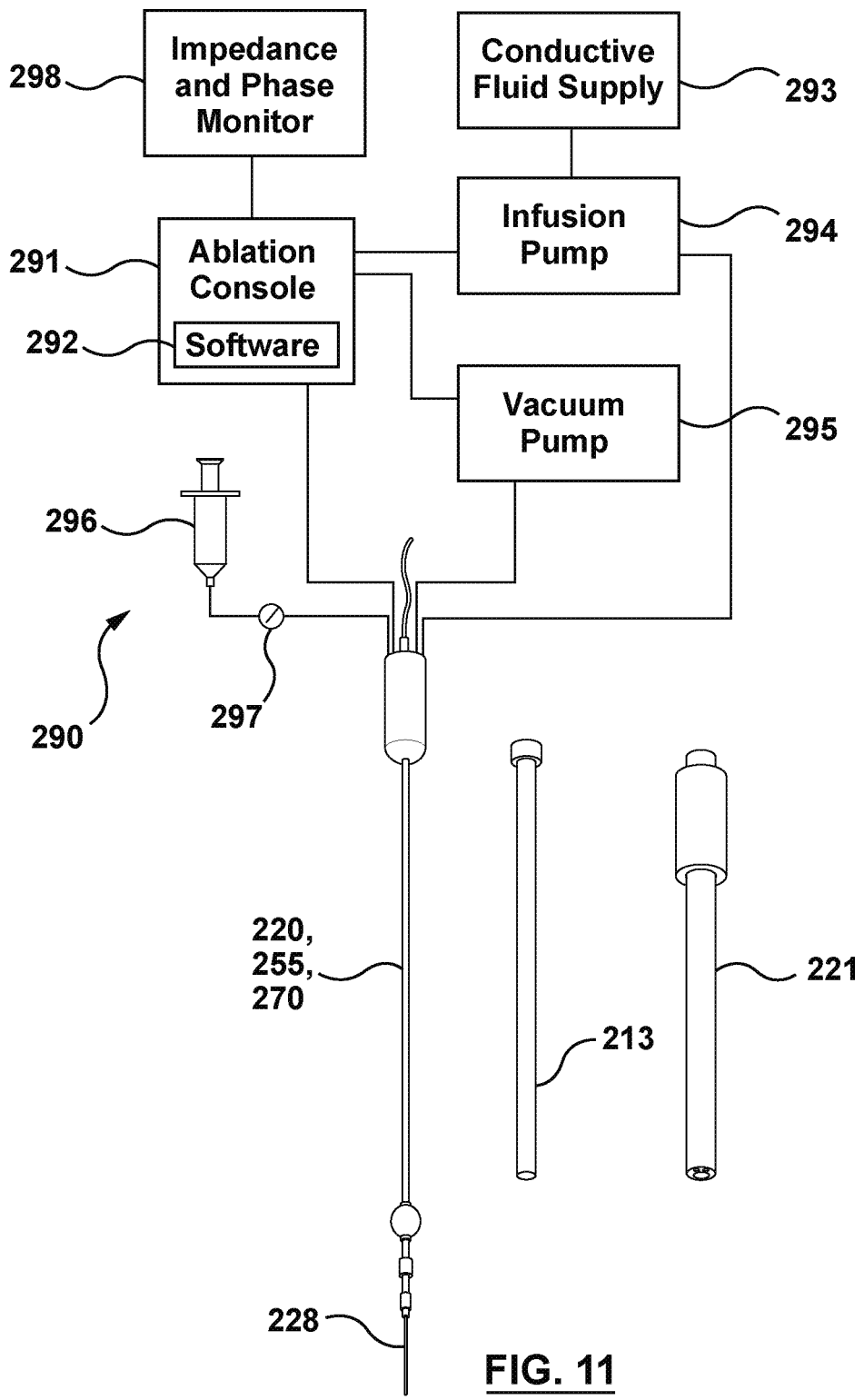
FIG. 11 is a schematic illustration of a system for operating endobronchial lung tumor ablation devices.

Devices for Endobronchial lung tumor ablation such as those disclosed herein (e.g., device 220, 255, or 270) may be part of a system 290 as shown in FIG. 11 further comprising an computerized ablation energy (e.g., RF) console 291 comprising a programmable controller with software 292, a conductive fluid supply 293 and infusion pump 294, a vacuum pump 295, an obturator inflator 296 (e.g., insulflator or syringe with valve 297) and associated connector cables and tubes to connect the proximal region of the device to the console, infusion pump, or vacuum pump.

Optionally, the system 290 may include more than one ablation device for example multiple ablation devices 100 and 101 deliverable through an occlusion catheter 270 as shown in FIG. 9, or multiple ablation devices such as 220 or 255. The system 290 may also include a guidewire 227, a delivery sheath 213, a dispersive grounding pad, or a bronchoscope 221. The ablation console 291 may further comprise an impedance and phase monitoring circuit and software 298 that is connectable to electrodes on ablation device (220, 255, 270), measures impedance and phase and displays their values to user. Optionally, an impedance and phase monitoring circuit and software 298 may be in a separate component, which may be connected to the ablation console to input measured impedance or phase to control algorithms of the Ablation console software 292.

The software 292 may include an algorithm that controls the vacuum pump 295 to remove air from the targeted lung portion. The vacuum pump may have a pressure sensor that indicates the difference in pressure between atmosphere and the targeted lung portion. The vacuum pump may apply a maximum negative pressure difference in a range of 1 to 5 atm and the algorithm may input the pressure difference and shut off the vacuum pump when the pressure difference is greater than the maximum negative pressure difference, at which time the vacuum pump may be signalled to seal air flow from the lung portion. In embodiments wherein the conductive fluid is infused through the same lumen through which air is removed from the lung, the system may have an automatically controlled switching valve that switches fluid communication from the vacuum pump to infusion pump, for example once the algorithm detects sufficient lung portion collapse either via pressure sensor signal or tissue impedance and phase associated with the distal and proximal electrodes on the device (e.g., 220, 255, or 270). For example, the software 292 may control the ablation console 291 to deliver electrical waveforms to the distal and proximal electrode to monitor tissue impedance or phase during operation of the vacuum pump 295 and control the vacuum pump to stop when an impedance drop signifies lung collapse. The software 292 may control the infusion pump 294 to pump conductive fluid from the fluid supply 293 to the device and into the targeted lung portion and optionally may deliver electrical waveforms to concurrently monitor impedance or phase to assess infusion. Optionally, infusion may continue (e.g., at a rate of about 5 mL/min) during delivery of ablation energy from the console 291. The software 292 may further control ablation energy delivery profiles including safety monitoring of temperature and impedance.

Optionally, the software 292 may control rate of infusion of conductive fluid (e.g., via infusion pump speed) during delivery of ablation energy based on electrode temperature feedback from a temperature sensor (e.g., 242, 262) to obtain a temperature set point. For example, a constant power may be delivered and a constant infusion flow rate may be delivered and as a temperature set point is approached power, flow rate or a combination of both may be titrated to achieve the temperature set point. If actual electrode temperature is below the set point, infusion rate may be decreased and/or power may be increased. If actual electrode temperature is above the set point, infusion rate may be increased and/or power may be decreased.

A conductive fluid such as hypertonic saline may have a boiling temperature higher than 100° C., which may allow greater ablation energy to be deposited into the conductive fluid as well as a higher fluid temperature to facilitate ablation of target tissue. This may be particularly valuable when delivering thermal and electrical energy through cartilaginous airway walls to ablate a tumor, since the airway walls have a relatively low thermal and electrical conductivity and tumor ablation requires a large ablation. For example, a conductive fluid such as 20% hypertonic saline may have a boiling temperature in a range of about 105° C. to 110° C.

It may be advantageous to generate steam in an occluded target region of a lung by raising the temperature of the conductive fluid that is injected in the region close to its boiling point. Generating steam and trapping it in the target region of the lung with the occluding device (e.g., balloon) may increase the vapor pressure of the conductive fluid and, thereby, further raise its boiling point, which may allow greater ablation energy to be delivered. Exposing the airway cartilaginous wall to temperatures around 100° C. for an extended period of time, for example 2 to 10 minutes, provides the advantage of softening its consistency and of allowing conductive fluid to better infiltrate and advance towards the targeted lung tissue. Furthermore, when lung parenchyma is heated, it shrinks and airways connected to the parenchyma are pulled closer together. Steam produced in a targeted lung region may pass to the associated parenchyma and shrink it prior to or during delivery of ablation energy, which may improve effectiveness of tumor ablation. An energy delivery console may comprise an energy delivery control algorithm that allows temperature set point that is within a close range about the boiling point of the conductive fluid at the pressure of the fluid in the target region. Optionally, an algorithm may have a steam-producing phase that delivers energy with a temperature set point suitable to generate steam (e.g., if 20% hypertonic saline is the conductive fluid, a temperature set point for a steam-producing phase may be in a range of 100° C. to 110° C., preferably around 105° C.). The ablation of targeted lung tissue may be performed at such increased temperature setpoint and last for a duration of 1 to 10 minutes. Alternatively, the steam-producing phase may have a predefined duration (e.g., up to 2 minutes) or be controlled by monitoring impedance between electrodes in which spikes of high impedance may indicate steam production. Yet alternatively, phases of steam production may be alternated with ablation phases of decreased temperature set points. For example, energy delivery in the first 2 minutes may be performed with a 105° C. set point, in the subsequent 2 minutes with an 85° C. set point, in the subsequent 2 minutes with a 105° C. set point and so on until the ablation duration (e.g., a total duration in a range of 8 to 15 minutes or about 10 minutes) expires or the therapeutic goal is achieved (e.g. moving average impedance increases over a targeted threshold). Optionally, a pressure sensor on the distal region of the device may be used to input a pressure signal to the controller and a rise in pressure can indicate adequate steam production. Optionally, a steam-producing phase may involve heating the conductive fluid by delivering ablation energy from the ablation elements or alternatively by delivering thermal energy from a direct heat resistive coil positioned on the device distal to the occluding device. A direct heat resistive coil may be an electrically resistive metal with an electrical insulation (e.g., polyimide, Parylene) coiled around the device shaft, which heats the conductive fluid by thermal conduction only. A steam-producing phase may be followed by a tumor ablation phase that may have a temperature set point that is lower than the set point of the steam-producing phase, as presented above.

When a conductive fluid is injected to the target region, a control algorithm may use a target set temperature in a range of 95° C. to 110° C., preferably 105° C., to remain below the boiling point of the conductive fluid. Alternatively, it may be desired to generate steam in the occluded target region in which case a set temperature may be in a range of 105° C. to 115° C., provided that sufficient safety mechanisms are designed into the system, such as fast RF energy shut-offs triggered by rapidly rising impedance, temperature or sudden changes in the electrical phase (i.e., the phase between the ablating current and ablating voltage).

The system(s), catheter(s) and apparatus described above and/or claimed may use at least one controller. This controller may comprise a digital processor (CPU) with memory (or memories), an analogical type circuit, or a combination of one or more digital processing units with one or more analogical processing circuits. In the present description and in the claims, it is indicated that the controller is "configured" or "programmed" to execute certain steps. This may be achieved in practice by any means which allow configuring or programming the controller. For instance, in case of a controller comprising one or more CPUs, one or more programs are stored in an appropriate memory. The program or programs containing instructions which, when executed by the controller, cause the controller to execute the steps described and/or claimed in connection with the controller. Alternatively, if the controller is of an analog type, then the circuitry of the controller is designed to include circuitry configured, in use, to process electric signals, such as to then execute the controller steps herein disclosed and/or claimed.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method to treat a human patient comprising:
    advancing a catheter through a natural airway of the patient and positioning a distal portion of the catheter in the natural airway of a lung of the patient at a target region in the lung,
    injecting a conductive hypertonic saline solution having a concentration of at least 5% of sodium chloride by weight/volume from the distal portion of the catheter into the target region, wherein the injecting of the conductive hypertonic saline solution injects no more than 20 ml of the conductive hypertonic saline solution into the target region;
    delivering energy from the distal portion into the conductive hypertonic saline solution in the target region, wherein the energy heats the conductive hypertonic saline solution in the portion of the airway, and
    ablating the target region with the energy delivered from the distal portion.

2. The method of claim 1, wherein the catheter is an endobronchial ablation catheter including a flexible shaft and the distal portion is on the flexible shaft, and
    wherein the advancing the catheter includes advancing the flexible shaft through a trachea of the patient and a bronchus of the lung and into a bronchi of the lung extending into the target region.

3. The method of claim 1, wherein the delivery of energy includes delivering radiofrequency electrical current from an ablation electrode on the distal portion of the catheter and into the conductive hypertonic saline solution.

4. The method of claim 1, wherein the distal portion of the catheter includes an ablation electrode connectable to a source of radio frequency electrical current, a fluid outlet connectable to a source of the conductive hypertonic saline solution, and an occluder proximal to the ablation electrode and the liquid outlet,
    wherein the method further comprises expanding the occluder in the natural airway to obstruct the natural airway proximal to the target region.

5. The method of claim 4, wherein a distance along the flexible shaft between the occluder and the ablation electrode is in a range of 5 to 20 mm.

6. The method of claim 4, wherein the ablation electrode has a length in a range of 3 to 20 mm.

7. The method of claim 4, wherein the ablation electrode is a first ablation electrode and the distal portion of the flexible shaft further comprises a second ablation electrode, wherein a distance between the first and second ablation electrodes along the distal portion is in a range of 5 to 15 mm.

8. The method of claim 1, wherein the flexible shaft has an outer diameter less than 2 mm and is configured to bend to a radius of curvature of less than 2.5 cm.

9. The method of claim 1, wherein the conductive hypertonic saline solution has a concentration of at least 23% of sodium chloride by weight/volume.

10. The method of claim 1, wherein the conductive hypertonic saline solution has a concentration of at least 20% of sodium chloride by weight/volume.

11. The method of claim 1, wherein the injecting of the conductive hypertonic saline solution is at a rate of no greater than 5 ml/min during the delivering of the energy.

12. A method for treating a patient with lung cancer comprising:
    advancing a catheter through a natural airway of a patient to a target region in a lung of the patient, wherein the target region has been identified as cancerous;
    expanding an occluder in the natural airway, wherein the occluder is mounted on the catheter;
    injecting a hypertonic saline solution having a concentration of at least 5% of sodium chloride by weight/volume of the hypertonic saline solution, wherein the hypertonic saline solution is injected from a fluid outlet in the catheter into the target region, wherein the occluder is proximal to the fluid outlet and prevents the hypertonic saline solution entering portions of the natural airway proximal to the occluder;
    delivering energy to a distal section of the catheter in the target region to heat the distal section to a range of 75 degrees Celsius to 105 degrees Celsius, and
    ablating the target region with the heated distal section in the target region.

13. The method of claim 12, wherein the ablative thermal energy is delivered from an electrode on the catheter distal to the occluder, and the electrode is a distance from the occuluder in a range of 5 to 20 mm.

14. A method for treating a patient with lung cancer comprising:
    advancing a catheter through a natural airway of a patient to a target region in a lung of the patient, wherein the target region has been identified as cancerous;
    expanding an occluder in the natural airway, wherein the occluder is mounted to the catheter;
    injecting a conductive hypertonic saline solution having a concentration of at least 5% of sodium chloride by weight/volume of the hypertonic saline solution, and the hypertonic saline solution is injected from a fluid outlet in the catheter into the target region;
    compressing the lung at the target region prior to the injection of the conductive hypertonic saline solution,
    delivering energy to the catheter in the portion of the airway wherein the energy heats the catheter to a range of 75 degrees Celsius to 105 degrees Celsius, and
    ablating the target region with the energy in the target region.

15. The method of claim 14, wherein the compressing of the lung includes removing a fluid from the target region prior to the injection of the hypertonic saline solution.

16. The method of claim 14, wherein the catheter is an endobronchial ablation catheter including a flexible shaft, and
    wherein the advancing the catheter includes advancing the flexible shaft through a trachea of the patient and a bronchus of the lung, and into a bronchi of the lung extending to the target region.

17. The method of claim 12, wherein the delivery of energy includes delivering radiofrequency (RF) electrical current from an ablation electrode on the catheter and into the conductive hypertonic saline solution injected into the target region.

18. The method of claim 12, wherein the injecting of the conductive hypertonic saline solution injects no more than 20 ml of the conductive hypertonic saline solution into the target region.

19. The method of claim 18, wherein the injecting of the conductive hypertonic saline solution is at a rate of no greater than 5 ml/min during the delivering of the energy.

20. The method of claim 12, wherein the conductive hypertonic saline solution has a concentration of at least 23% of sodium chloride by weight/volume.

21. The method of claim 12, wherein the conductive hypertonic saline solution has a concentration of at least 20% of sodium chloride by weight/volume.

22. A method for treating a patent having a lung tumor comprising:
   advancing an extended working channel of a bronchoscope transbronchially towards a natural airway of a lung of the patient;
   advancing an ablation catheter from the extended working channel, through a bronchi of the natural airway proximate to a target region of the lung including the lung tumor;
   expanding a balloon on the ablation catheter to occlude the bronchi;
   injecting a conductive hypertonic saline solution having a concentration of at least 5% of sodium chloride by weight/volume from the catheter into the target region, wherein the balloon suppresses the hypertonic saline solution flowing past the balloon towards a portion of the bronchi proximal to the balloon; and
   delivering radiofrequency (RF) electrical current from an ablation electrode on the ablation catheter to ablate lung tissue in the target region.

23. The method of claim 22, wherein the application of the RF electrical current heats the ablation electrode to a range of 75 degrees Celsius to 105 degrees Celsius.

24. The method of claim 22, further comprising compressing lung tissue at the target region immediately prior to the injection of the conductive hypertonic saline solution.

25. The method of claim 22, wherein the ablation electrode has a length in a range of 3 to 20 mm.

26. The method of claim 22, wherein the ablation electrode is a first ablation electrode and the distal portion of the flexible shaft further comprises a second ablation electrode, wherein a distance between the first and second ablation electrodes along the distal portion is in a range of 5 to 15 mm.

27. The method of claim 22, wherein the ablation catheter has an outer diameter less than 2 mm and is configured to bend to a radius of curvature of less than 2.5 cm.

28. The method of claim 22, wherein the injecting of the conductive hypertonic saline solution injects no more than 20 ml of the conductive hypertonic saline solution into the target region.

29. The method of claim 28, wherein the injecting of the conductive hypertonic saline solution is at a rate of no greater than 5 ml/min during the delivering of the energy.

30. The method of claim 22, wherein the conductive hypertonic saline solution has a concentration of at least 23% of sodium chloride by weight/volume.

31. The method of claim 22, wherein the conductive hypertonic saline solution has a concentration of at least 20% of sodium chloride by weight/volume.

32. The method of claim 22, wherein a distance between the balloon and the ablation electrode is in a range of 5 mm to 20 mm.

\* \* \* \* \*